US012653582B2

(12) United States Patent
Haschtmann et al.

(10) Patent No.: US 12,653,582 B2
(45) Date of Patent: Jun. 16, 2026

(54) CONNECTOR IMPLANT FOR EXTENDING A SPINAL CONSTRUCT

(71) Applicant: INNO4SPINE AG, Stans (CH)

(72) Inventors: Daniel Haschtmann, Küsnacht (CH); Heiko Koller, Kufstein (AT); Dezső János Jeszenszky, Küsnacht (CH); Tamás Fülöp Fekete, Zürich (CH); Tom Overes, Biberist (CH)

(73) Assignee: INNO4SPINE AG, Stans (CH)

( * ) Notice: Subject to any disclaimer, the term of this patent is extended or adjusted under 35 U.S.C. 154(b) by 326 days.

(21) Appl. No.: 17/793,586

(22) PCT Filed: Dec. 8, 2020

(86) PCT No.: PCT/IB2020/061632
§ 371 (c)(1),
(2) Date: Jul. 18, 2022

(87) PCT Pub. No.: WO2021/144636
PCT Pub. Date: Jul. 22, 2021

(65) Prior Publication Data
US 2023/0048510 A1      Feb. 16, 2023

(30) Foreign Application Priority Data

Jan. 19, 2020    (CH) .................................... 00056/20

(51) Int. Cl.
*A61B 17/70* (2006.01)

(52) U.S. Cl.
CPC ...... *A61B 17/7049* (2013.01); *A61B 17/7002* (2013.01)

(58) Field of Classification Search
CPC .............. A61B 17/705; A61B 17/7049; A61B 17/7052
See application file for complete search history.

(56) References Cited

U.S. PATENT DOCUMENTS 5,630,816 A * 5/1997 Kambin ............. A61B 17/7052
606/252
2002/0138077 A1* 9/2002 Ferree ................ A61B 17/7014
606/259

(Continued)

FOREIGN PATENT DOCUMENTS

CN          110680488 A      1/2020
EP          2087847 A1 *    8/2009    ........... A61B 17/705

(Continued)

OTHER PUBLICATIONS

Swiss Search Report dated Mar. 2, 2020 as received in application No. 00056/20.

(Continued)

*Primary Examiner* — Eduardo C Robert
*Assistant Examiner* — Anna V. Little
(74) *Attorney, Agent, or Firm* — Maschoff Brennan

(57) ABSTRACT

It is an object of the present invention to overcome at least some of the problems associated with elongating an existing pedicle screw and rod construct. To this end, there is proposed a spinal rod assembly for elongating an in situ spinal posterior rod system by connecting the spinal rod construct to a head of an in situ bone fastener. The spinal rod assembly according to one embodiment comprises a rod connector and at least one rod fastener, wherein the rod connector comprises a first connector head and a second connector head, connected by an elongated bar, and forming a space between the first and second connector heads. The first connector head comprises a first pocket for receiving a first rod end, while the second connector head comprises a second pocket for receiving a second rod end.

10 Claims, 18 Drawing Sheets

(56) References Cited

U.S. PATENT DOCUMENTS

| | | | | | |
|---|---|---|---|---|---|
| 2006/0229611 | A1* | 10/2006 | Avery | ................. | A61B 17/705 606/279 |
| 2006/0247627 | A1* | 11/2006 | Farris | ................. | A61B 17/705 606/280 |
| 2007/0179501 | A1* | 8/2007 | Firkins | ................ | A61B 17/705 606/254 |
| 2008/0021455 | A1* | 1/2008 | Chao | ................. | A61B 17/7037 606/250 |
| 2008/0027436 | A1* | 1/2008 | Cournoyer | ........ | A61B 17/7079 606/86 A |
| 2008/0215095 | A1* | 9/2008 | Biedermann | ...... | A61B 17/7031 606/246 |
| 2008/0234743 | A1* | 9/2008 | Marik | ................ | A61B 17/705 606/257 |
| 2008/0262553 | A1* | 10/2008 | Hawkins | ........... | A61B 17/7049 606/151 |
| 2009/0093847 | A1* | 4/2009 | Wilcox | ............... | A61B 17/705 606/301 |
| 2010/0114167 | A1* | 5/2010 | Wilcox | ............... | A61B 17/705 606/264 |
| 2010/0292736 | A1* | 11/2010 | Schwab | .............. | A61B 17/705 606/279 |
| 2011/0087287 | A1* | 4/2011 | Reeder, Jr. | ........ | A61B 17/7011 606/264 |
| 2011/0106166 | A1* | 5/2011 | Keyer | ................ | A61B 17/7034 606/279 |
| 2013/0018421 | A1* | 1/2013 | George | ................. | A61B 17/88 29/428 |
| 2013/0204302 | A1 | 8/2013 | Rezach et al. | | |
| 2014/0066989 | A1* | 3/2014 | Mundis | ............. | A61B 17/7079 606/279 |
| 2017/0100167 | A1* | 4/2017 | Lange | ................. | A61B 17/705 |
| 2019/0183539 | A1 | 6/2019 | Di Lauro | | |

FOREIGN PATENT DOCUMENTS

| | | | | | |
|---|---|---|---|---|---|
| JP | | 2001309924 A | * | 11/2001 | ........... A61B 17/705 |
| KR | | 102023127 B1 | | 9/2019 | |
| WO | | 2010120989 A1 | | 10/2010 | |
| WO | | WO-2012024335 A2 | * | 2/2012 | ......... A61B 17/7014 |
| WO | | 2019117251 A1 | | 6/2019 | |

OTHER PUBLICATIONS

EP Office Action dated Jun. 25, 2024 as received in Application No. 20825247.8.

* cited by examiner

80c

60b

60a

60d

10

80c

50a

A1 & A2 & A3

80d    50b

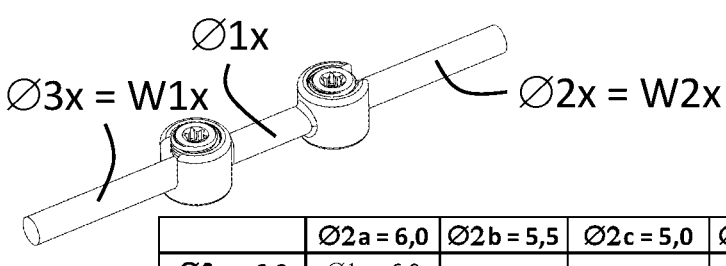
|  | Ø2a = 6,0 | Ø2b = 5,5 | Ø2c = 5,0 | Ø2d = 4,5 | Ø2e = 4,0 | Ø2f = 3,5 |
|---|---|---|---|---|---|---|
| Ø3a = 6,0 | Ø1a = 6,0 |  |  |  |  |  |
| Ø3b = 5,5 |  | Ø1b = 5,5 |  |  |  |  |
| Ø3c = 5,0 |  |  | Ø1c = 5,0 |  |  |  |
| Ø3d = 4,5 |  |  |  | Ø1d = 4,5 |  |  |
| Ø3e = 4,0 |  |  |  |  | Ø1e = 4,0 |  |
| Ø3f = 3,5 |  |  |  |  |  | Ø1f = 3,5 |
FIG. 4C
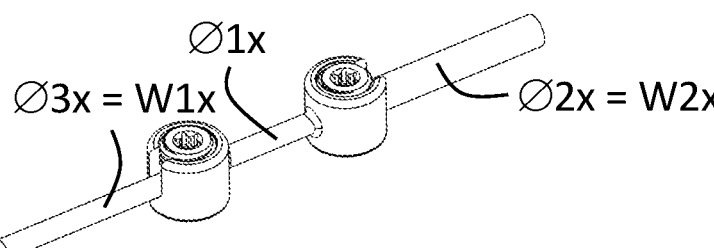
|  | Ø2a = 6,0 | Ø2b = 5,5 | Ø2c = 5,0 | Ø2d = 4,5 | Ø2e = 4,0 | Ø2f = 3,5 |
|---|---|---|---|---|---|---|
| Ø3a = 6,0 |  |  |  |  |  |  |
| Ø3b = 5,5 | Ø1a = 6,0 |  |  |  |  |  |
| Ø3c = 5,0 | Ø1a = 6,0 | Ø1b = 5,5 |  |  |  |  |
| Ø3d = 4,5 | Ø1a = 6,0 | Ø1b = 5,5 | Ø1c = 5,0 |  |  |  |
| Ø3e = 4,0 | Ø1a = 6,0 | Ø1b = 5,5 | Ø1c = 5,0 | Ø1d = 4,5 |  |  |
| Ø3f = 3,5 | Ø1a = 6,0 | Ø1b = 5,5 | Ø1c = 5,0 | Ø1d = 4,5 | Ø1e = 4,0 |  |
FIG. 4D
|  | Ø2a = 6,0 | Ø2b = 5,5 | Ø2c = 5,0 | Ø2d = 4,5 | Ø2e = 4,0 | Ø2f = 3,5 |
|---|---|---|---|---|---|---|
| Ø3a = 6,0 |  | Ø1b = 5,5 | Ø1c = 5,0 | Ø1d = 4,5 | Ø1e = 4,0 | Ø1f = 3,5 |
| Ø3b = 5,5 |  |  | Ø1c = 5,0 | Ø1d = 4,5 | Ø1e = 4,0 | Ø1f = 3,5 |
| Ø3c = 5,0 |  |  |  | Ø1d = 4,5 | Ø1e = 4,0 | Ø1f = 3,5 |
| Ø3d = 4,5 |  |  |  |  | Ø1e = 4,0 | Ø1f = 3,5 |
| Ø3e = 4,0 |  |  |  |  |  | Ø1f = 3,5 |
| Ø3f = 3,5 |  |  |  |  |  |  |
FIG. 4E

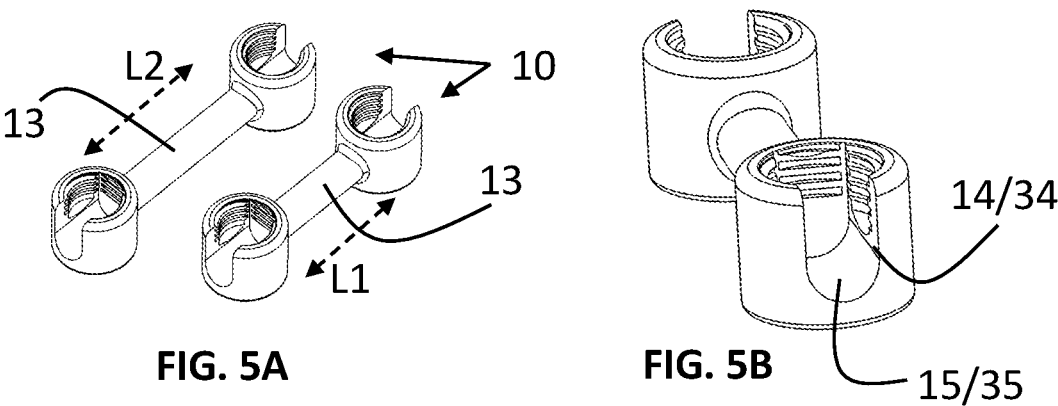
FIG. 5A                    FIG. 5B
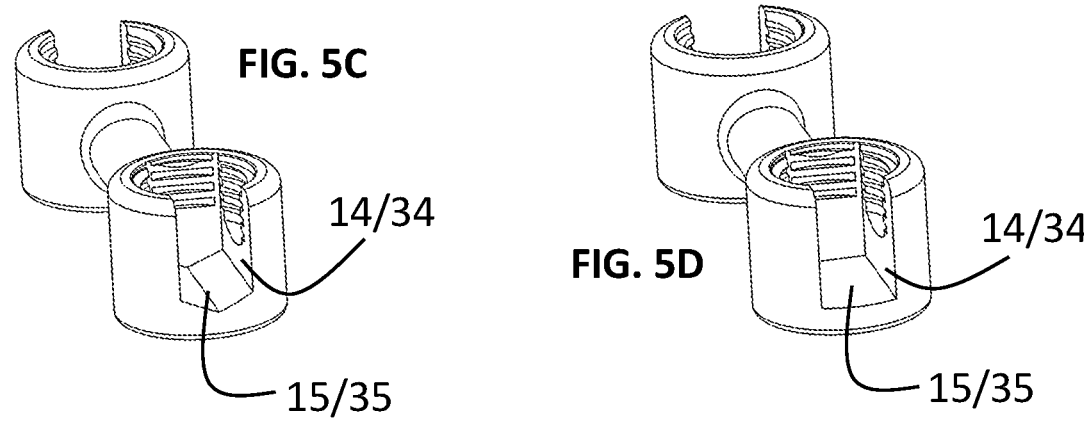
FIG. 5C
FIG. 5D
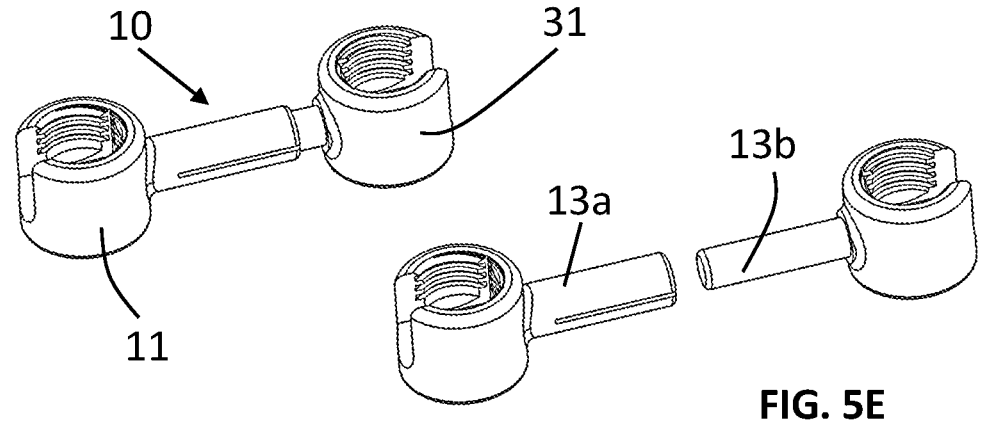
FIG. 5E

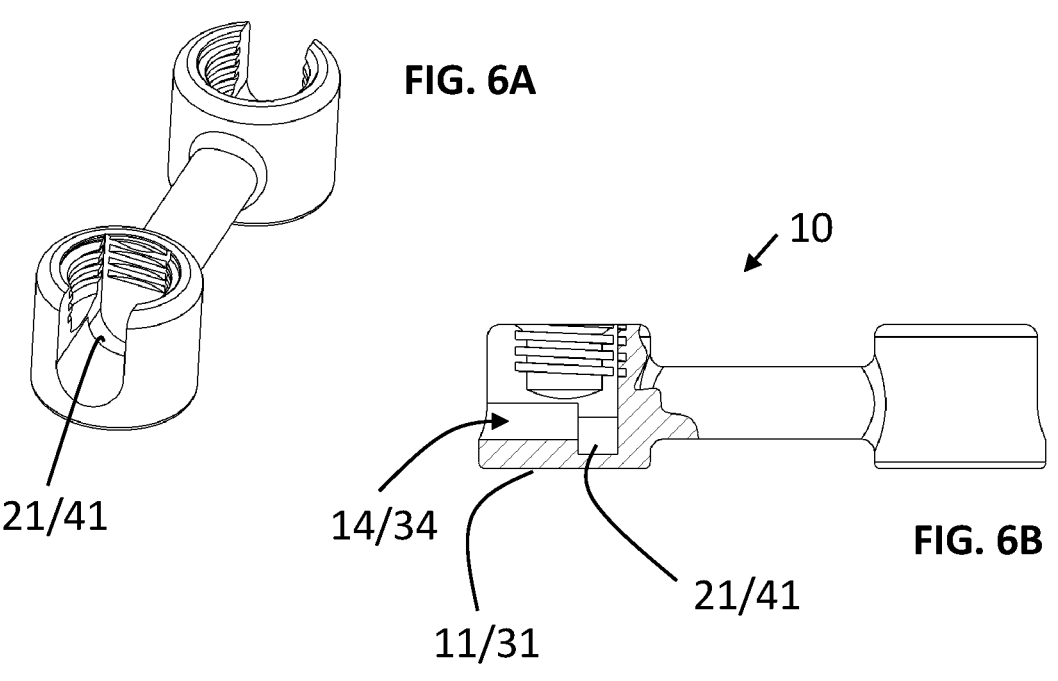
FIG. 6A
21/41
10
14/34
11/31
21/41
FIG. 6B
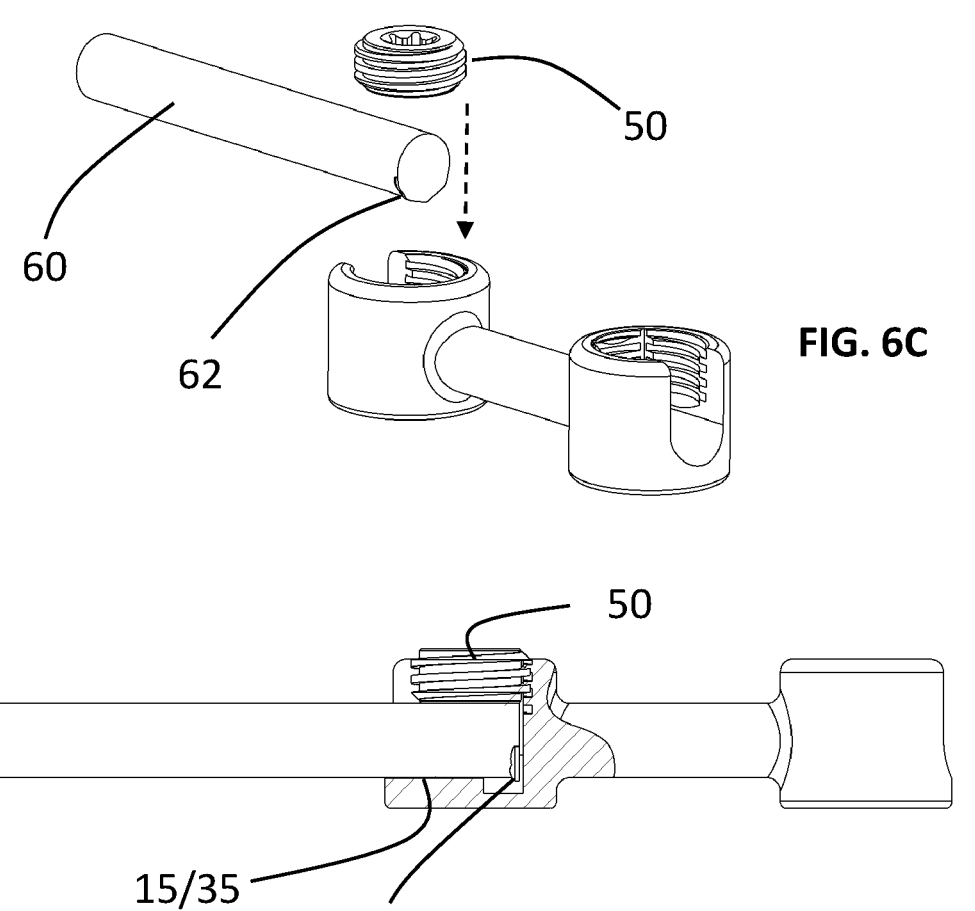
50
60
62
FIG. 6C
50
15/35
62     FIG. 6D

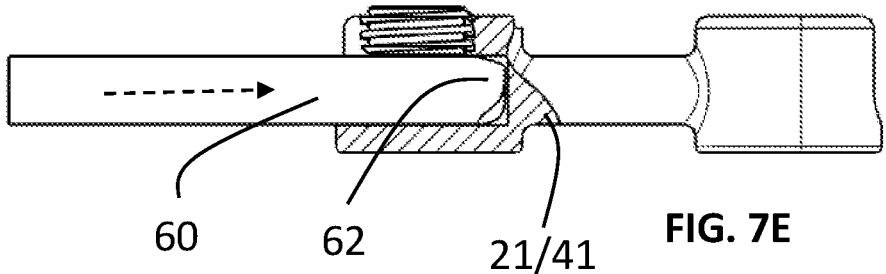
60     62     21/41     FIG. 7E
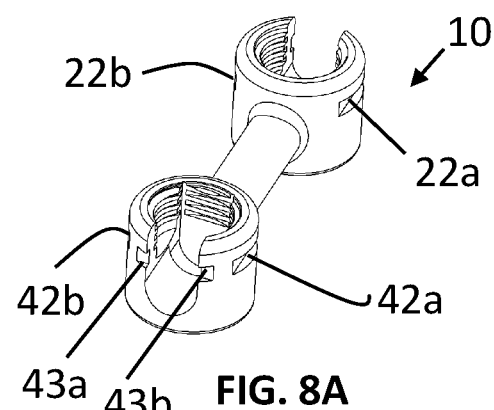
22b     10     22a     42b     42a     43a  43b     FIG. 8A
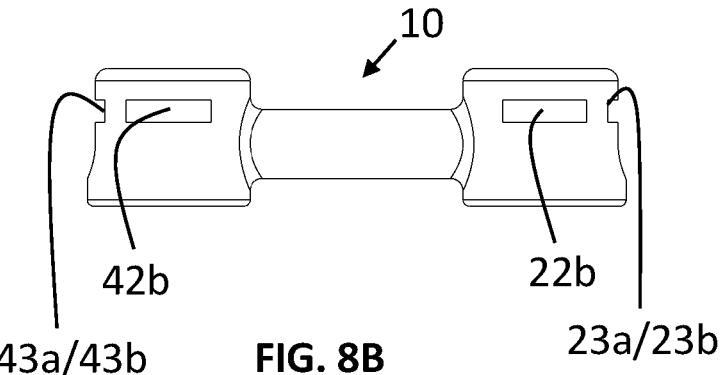
10     42b     22b     43a/43b     FIG. 8B     23a/23b

FIG. 9E

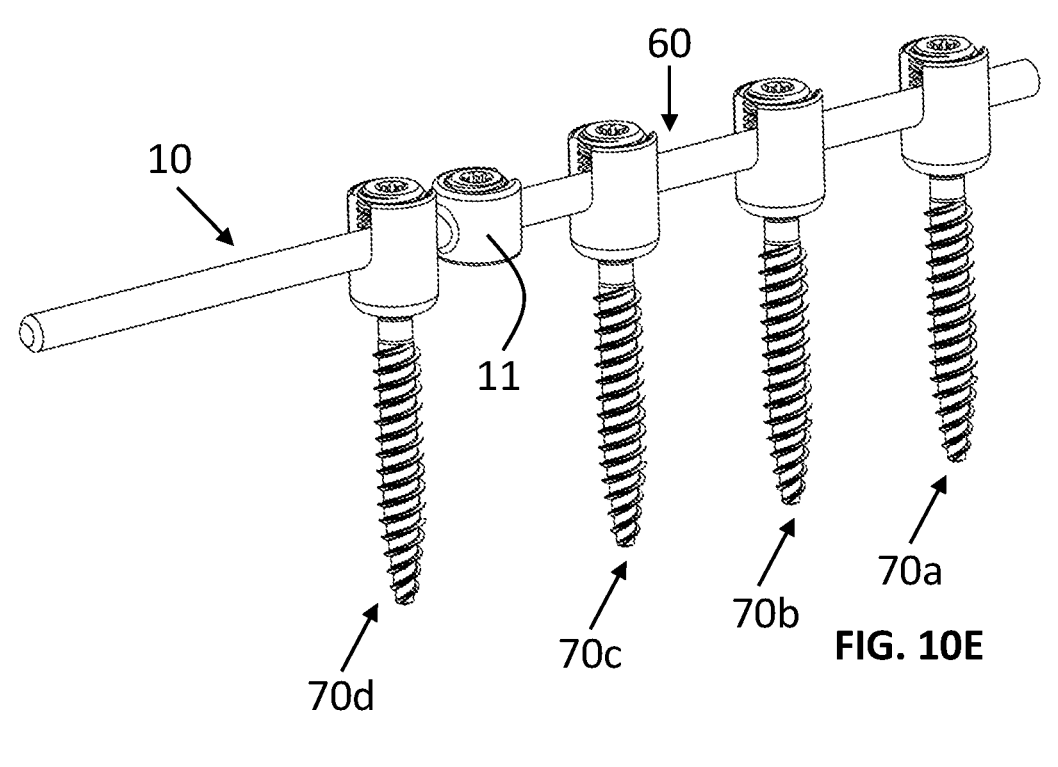
FIG. 10E
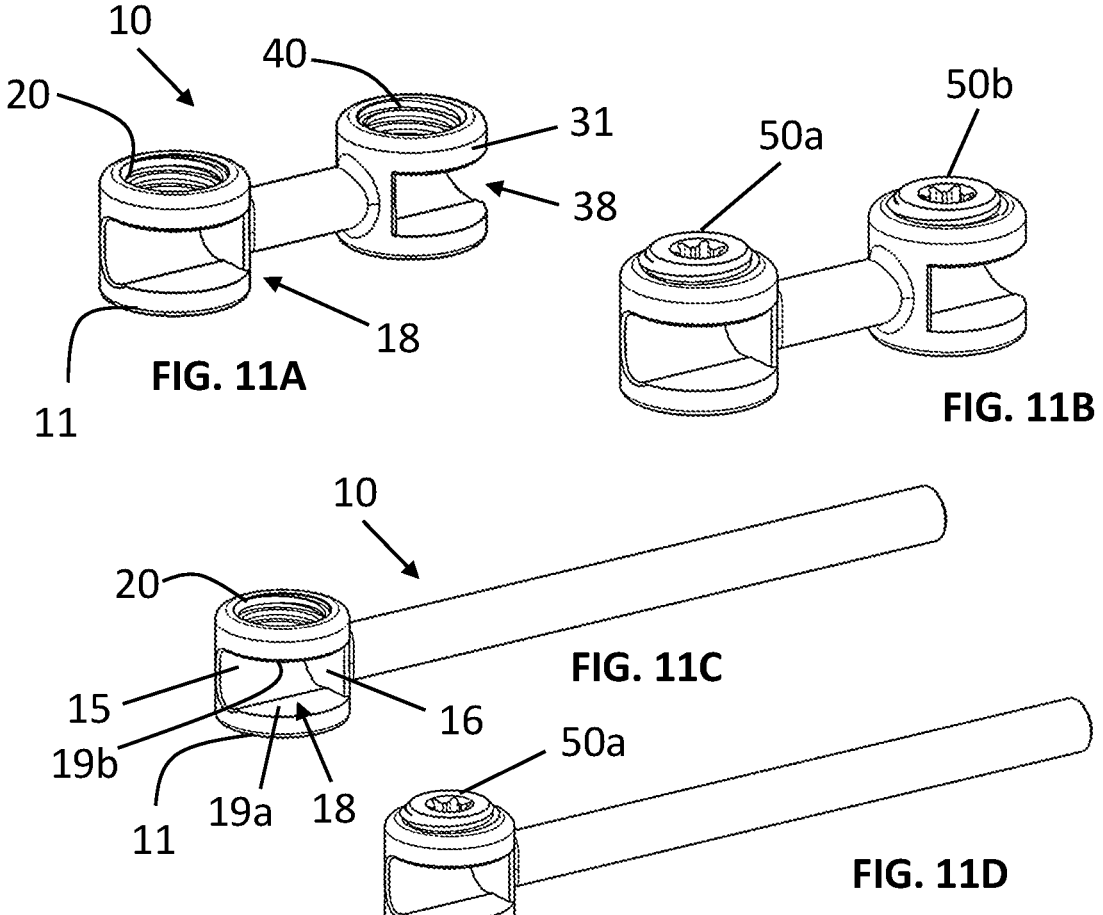
FIG. 11A
FIG. 11B
FIG. 11C
FIG. 11D

CONNECTOR IMPLANT FOR EXTENDING A SPINAL CONSTRUCT

TECHNICAL FIELD OF THE INVENTION

The present invention relates to a spinal rod assembly for elongating an in situ spinal posterior rod system. A bone fastener, most commonly a pedicle screw, may be connected to the spinal rod assembly. The bone fastener may comprise a tulip head for receiving a spinal rod connector of the spinal rod assembly. The invention also relates to a method for connecting the spinal rod assembly to an existing posterior spinal construct (comprising an in situ pedicle screw), and for connecting to an additional spinal rod. The invention further relates to a kit containing multiple rod connectors enabling spinal rods of different diameters as well as rods of equal diameters to be connected.

BACKGROUND OF THE INVENTION

In orthopaedic surgery around the spine, posterior spinal stabilisation systems are often placed to a target site to realign, recorrect or stabilise the spinal column to compensate for malalignment caused by for example degeneration of the spine, born malalignments, such as excessive lordosis, kyphosis and scoliosis, and for example trauma, such as fractures.

Often a preplaced construct, or a construct in situ needs to be extended to different vertebral levels of the spinal column due to progression of the degeneration or disease. A construct is best extended in a substantial collinear orientation to the construct in situ. To be able to extend the system, according to common techniques, the full in situ rod is removed from the bone fasteners, and replaced by a rod of longer length. Removal is executed by unscrewing so-called setscrews that rigidly fix the rod into the tulip head of the bone fastener. The rod is pulled out after removal of all setscrews. In an additional surgical step, new bone fasteners are placed in the vertebral levels, to which the construct is intended to be elongated.

Now, the new rod of longer length is reattached to the bone fasteners that are in place, and additionally attached to newly placed bone fasteners. The removal of the old rod destabilises the spine during surgery, and requires a large skin and soft tissue access to the implants. Especially in the cases of longer constructs, this can be a very invasive surgery.

Alternatively, a new rod can collinearly be attached to the in situ rod. Also here the bone fasteners that are in place need to be manipulated. Some of the setscrews which fixate the in situ rod to the bone fasteners, need to be loosened, to lift the in situ rod, and to attach a rod extension. Also this procedure requires one or more large skin incisions and a soft tissue access to the implants. Especially in the cases of longer constructs, this can equally be a very invasive surgery.

In many cases such extensions need to take place in transition areas of the lumbar-to-thoracic and thoracic-to-cervical spine. Anatomically, the natural spine decreases in size from the lumbar spine to the cervical spine (from the lower back to the neck). Therefore, when extending a system towards the cervical spine, there is a need for connecting the system to smaller rods. In most common spinal stabilisation systems, this transition is made using intermediate connectors which allow a thinner rod to be placed next to a thicker rod. The transition is created by connecting the ends of a thicker rod and a thinner rod in a parallel manner, resulting in a more voluminous construct.

SUMMARY OF THE INVENTION

It is an object of the present invention to overcome at least some of the problems associated with elongating an existing pedicle screw and rod construct. A solution is needed that may obviate the need of removal of stable, existing, in situ pedicle screws, and that also provides the ability to connect an existing rod to rods of substantially identical and different diameters. Moreover, there is a need for a solution which forms an intermediate spinal connector, and which allows different systems of different suppliers to be rigidly connected.

According to a first aspect of the invention, there is provided a spinal rod connector assembly as recited in claim 1.

The proposed rod connector assembly has for instance the advantage that it helps the surgeon to substantially collinearly extend an existing in situ spinal rod of a first diameter without the necessity of removing the last bone fastener of the in situ construct while allowing attachment to a new rod of a second diameter.

According to a second aspect of the invention there is provided a kit of rod connectors.

The proposed kit has for instance the advantage that it helps the surgeon to substantially collinearly extend an existing in situ spinal rod of a first diameter without the necessity of removing the last bone fastener of the in situ construct while allowing attachment to a new rod of a second diameter. The kit contains at least a first rod connector and a second rod connector, where the first rod connector allows rods having a first diameter to be connected, and the second rod connector allows rods of a second, different diameter to be connected.

According to a third aspect of the invention there is provided a method of extending an in situ construct.

The proposed method allows a first rod to be connected to a second rod, wherein one rod has been previously implanted, and the second rod is attached thereto.

Other aspects of the invention are recited in the dependent claims attached hereto.

BRIEF DESCRIPTION OF THE DRAWINGS

Other features and advantages of the invention will become apparent from the following description of non-limiting example embodiments, with reference to the appended drawings, in which:

FIGS. 4A to 4E depict a kit of rod connectors, including multiple rod connectors allowing rods of equal or similar diameters as well as rods of different diameters to be connected;

FIGS. 5A to 5H depict in perspective views alternative designs of the rod connector, FIGS. 6A to 6D depict a second embodiment of the rod connector related to inaccurate cuts of a spinal rod;

FIGS. 7A to 7E depict a third embodiment of the rod connector related to inaccurate cuts of a spinal rod;

FIGS. 8A and B depict a fourth embodiment of the rod connector related to the ability to hold the rod connector with an instrument;

FIG. 9E shows an example kit with modular rod connectors;

FIGS. 10A to 10E show a further variant of the rod connector comprising only one connector head; and FIGS. 11A to 11H show a further variant of the rod connector.

DETAILED DESCRIPTION OF THE INVENTION

Figure 1A:
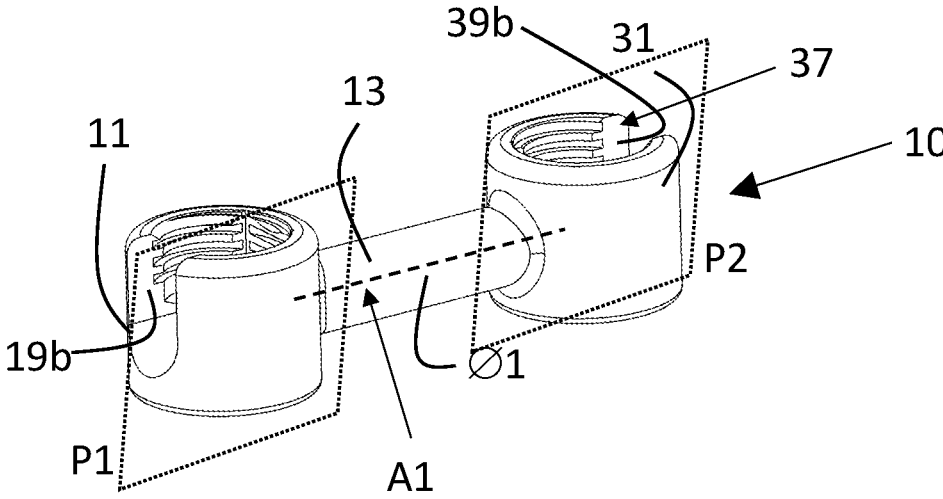
FIGS. 1A to 1C depict in perspective views an example rod connector according to an embodiment of the present invention.

The embodiments of the present invention will now be described in detail with reference to the attached figures. The embodiments are described in the context of extending or elongating an in situ posterior spinal construct. Although the invention is specifically described in the context of extending the posterior spinal construct, the teachings of the invention are not limited to this environment. The teachings of the present invention are equally applicable for extending rod-based stabilisation constructs for other bones. Identical or corresponding functional and structural elements which appear in the different drawings are assigned the same reference numerals. When the words first and second are used to refer to different elements, it is to be understood that this does not necessarily imply or mean that the first and second elements are somehow structurally substantially different elements or that their dimensions are substantially different unless specifically stated.

One example way of extending an in situ spinal construct is by adding at least two bone fasteners in adjacent vertebral bodies and elongating the spinal construct. Another example way of extending an in situ spinal construct is by adding at least one bone fastener in an adjacent vertebral body and elongating the spinal construct by previously cutting the in situ rod between the last two in situ bone fasteners, removing the cut-off rod end, and assembling the spinal connector in the last in situ bone fastener.

In situ in this context means already present or previously placed. The posterior spinal construct to be elongated therefore may have been placed in a previous surgical intervention, or was placed in the present surgical intervention.

A bone fastener in this context means an intermediate structural element, which can be brought into the target bone, and forms a stabile connection between the target bone and the remaining spinal construct. Most often a bone fastener is a fastening element, such as a screw.

Figure 1B:
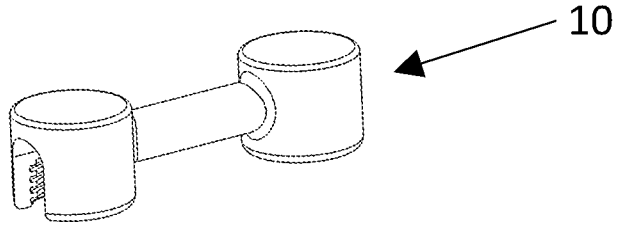
Figure 1C:
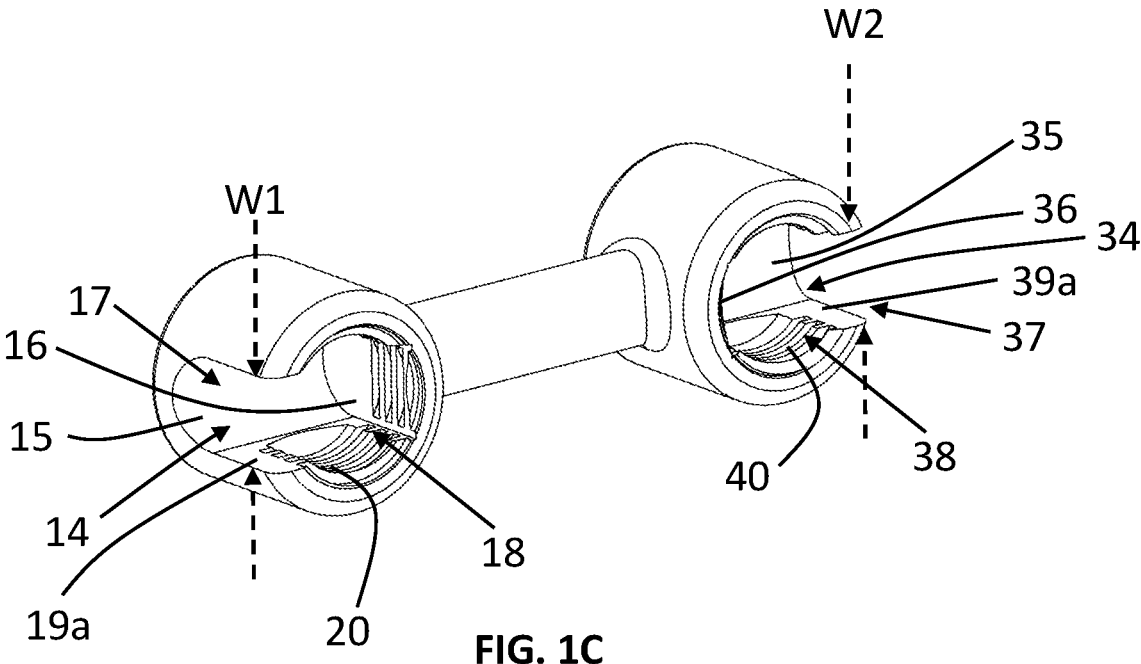

FIGS. 1A to 1C depict a rod connector 10 according to the first embodiment in perspective views. In this example embodiment, the rod connector 10 comprises one monolithic body, i.e., a body constructed from a single piece. As shown in FIGS. 1A to 1C, the rod connector comprises at least one first connector head 11, a second connector head 31, a connecting element, which in this example is a central or elongated bar 13 having a given length L1 and a diameter Øl or a circumference C1 connecting both heads to each other. In this example, the first and second connector heads are both substantially hollow or partially hollow cylindrical elements, which are located at the opposite ends of the elongated bar, which is a longitudinal, tubular element.

The first connector head 11 comprises a first pocket 14 having a first pocket bottom seat 15 (or first seat 15) and a first pocket end seat 16 (or second seat 16). In the present description, a seat may be understood to be a contact surface designed to be in direct or intimate contact with a spinal rod as explained later. In an example embodiment, as depicted, the pocket bottom seat and the end seat may be substantially orthogonally oriented, or more specifically the planes defined by the bottom pocket seat and the end seat. Alternatively, both seats may be oriented at an angle, such as between 60 and 120 degrees. The first pocket is open opposite to the first pocket seats 15, 16. Thus, the first pocket has a first end entrance or opening 17 and an intersecting or connected first top entrance or opening 18, allowing insertion of the spinal rod as explained later. The first pocket seats define a maximal placement depth for the rod to be placed into the pocket. The first pocket is further defined by first pocket sidewalls 19a, 19b. The side walls are spaced a certain distance apart, which defines a first pocket width W1 (minimal pocket width) defined at the level of the first end entrance 17. According to the present example embodiment, the first pocket 14 defines a first central plane P1 and the bar 13 defines a first central or length axis A1 (extending longitudinally across the bar), which are substantially aligned with each other. Moreover, the first pocket comprises a first internal locking feature 20, intersecting therewith, and extending from the first top entrance 18 towards the first pocket bottom seat 15. The first internal locking feature as shown in FIGS. 1A to 1C is configured as an internal thread, sized and shaped to engage in a threaded manner with a first rod fastener 50a as described in more detail later.

Similar to the first connector head 11, the second connector head 31 comprises a second pocket 34 having a second pocket bottom seat 35 (or third seat 35) and a second pocket end seat 36 (or fourth seat 36). The second pocket is open opposite to the second pocket seats 35, 36. Thus the second pocket has a second end entrance or opening 37 and an intersecting or connected second top entrance or opening 38, allowing insertion of the spinal rod as explained later. The second pocket seats define a maximal placement depth for the rod to be placed into the pocket. The second pocket is further defined by second pocket sidewalls 39a, 39b. The side walls are spaced a certain distance apart, which defines a second pocket width W2 (minimal pocket width) defined at the level of the second end entrance 37. According to the present example embodiment, the second pocket 34 defines a second central plane P2 such that it is substantially aligned with the first central axis A1. Moreover, the second pocket comprises a second internal locking feature 40, intersecting therewith, and extending from the second top entrance 38 towards the second pocket bottom seat 35. The second internal locking feature as shown in FIGS. 1A to 1C is configured as an internal thread, sized and shaped to engage in a threaded manner with a second rod fastener 50b as described in more detail later.

It is to be noted that the respective first or second plane P1, P2 divides the respective connector head into symmetrical halves. The first axis A1 can be considered to be an imaginary axis passing longitudinally through the centre of the elongated bar 13. It is further to be noted that the first and second central planes P1, P2 may not be parallel, and they may form an angle of 0-30 degrees with respect to each other. Furthermore, one or both of the central planes may be offset, e.g., 0-15 mm, with respect to the first central axis A1.

In the present description, the word circumference is used to describe the enclosing boundary (or its length) of a curved geometric figure or object. More specifically, the word outer circumference may be used to describe the circular enclosing boundary of a cylinder. Although in the present example the elongated bar is of a cylindrical shape, the word circumference is not limited to a circular boundary, but also defines a general distance around an object, such as a perimeter, border, boundary, periphery, etc. For instance, according to an example, the word circumference may describe the boundary of an oval shaped element. Other shapes such as polygons, irregular shapes also have an (average) external or internal boundary forming a circumference. Furthermore, in the present description, the word diameter does not imply the use of an element having a circular cross section. Thus, the word diameter may be understood to mean the greatest cross-sectional dimension of an object.

Figure 2A:
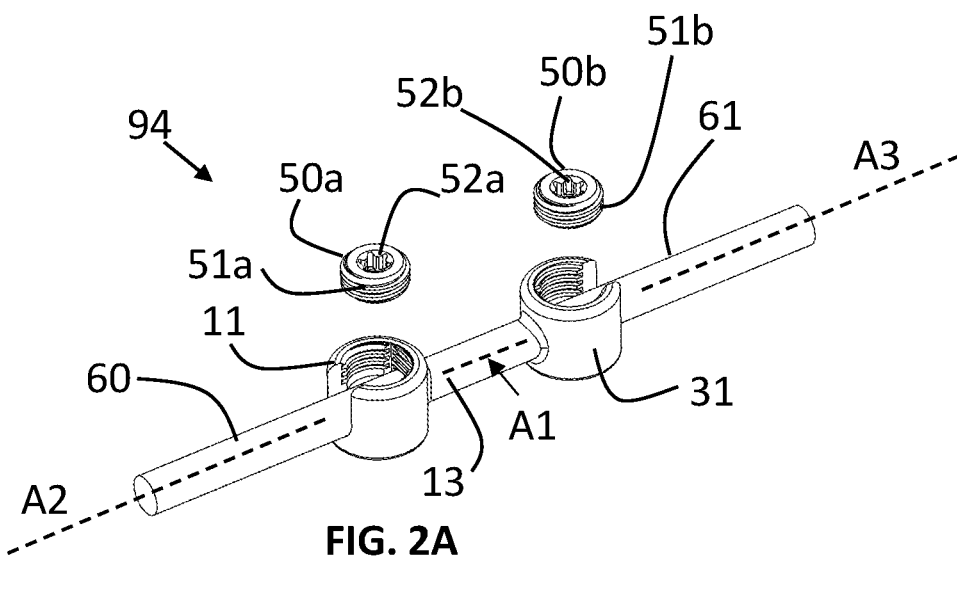
FIGS. 2A and 2B depict the process of connecting the rod connector of FIGS. 1A to 1C to a first rod and a second rod by using a first rod fastener and a second rod fastener, respectively.
Figure 2B:
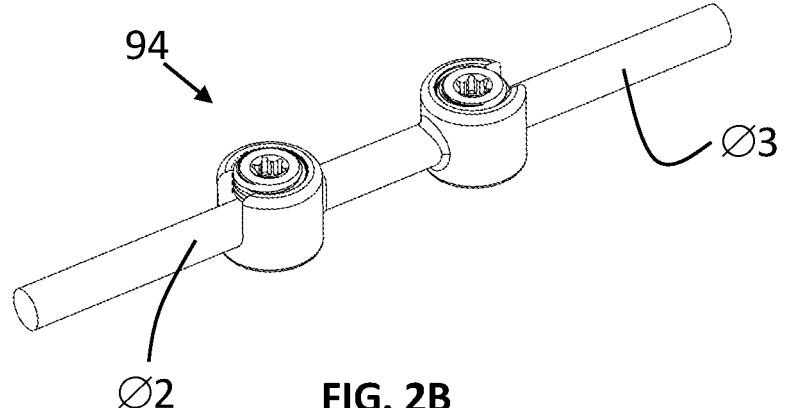

FIGS. 2A and 2B depict the rod connector 10 together with a first rod 60, a second rod 61 and first and second rod fasteners 50a, 50b. The rod connector 10 together with the first and/or second rod fasteners 50a, 50b can be considered to form a spinal rod assembly or construct 94. FIG. 2A illustrates the first and second rods 60, 61 in a position where they are placed in the first and second pockets 14, 34 of the rod connector 10, respectively. Thus, the respective pocket 14, 34 is sized and shaped to directly receive, or to indirectly receive by means of an insert in the respective pocket as explained later, the respective rod. The first and second rod fasteners 50a, 50b are aligned with the first and second internal locking features 20, 40 of the first and second connector heads 11, 31, respectively. The first rod fastener 50a comprises a first external locking feature or means 41a and a first drive 42a. The first drive 42a is intended to engage with a locking tool, providing a means to lock the first rod fastener into the first connector head. In the present embodiment, the first external locking means is shaped as an external thread.

Similar to the first rod fastener 50a, the second rod fastener 50b comprises a second external locking feature or means 51b and a second drive 52b. The second drive 52b is intended to engage with a locking tool, providing an instrument to lock the second rod fastener into the second connector head. In the present embodiment, the second external locking means is shaped as an external thread. In the present example, the first and second rod fasteners 50a, 50b are substantially identical elements.

FIG. 2B depicts the construct in an assembled state. More specifically, the first and second rod fasteners 50a, 50b are now threadedly engaged with the first and second pockets 14, 34, respectively. In this manner, the first and second rods are firmly connected to the rod connector 10 so that the first rod 60 is received or seated in the first pocket 14, while the second rod 61 is received or seated in the second pocket 34. However, as can be seen in FIG. 2B, the first and second rods protrude from their respective pockets. In other words, the rods are not completely received by the pockets.

As previously described, the respective rod fastener engages with the respective connector head and presses the respective rod against the bottom seat, simultaneously bordered by the side walls, and in this manner the rod can be rigidly fixated into the rod connector. Alternatively, the rod fastener may be placed over the head, therefore including an internal locking means sized and shaped to engage with an external locking feature of the connector head. In other words, the internal locking features of the connector heads may be shaped as external locking features, but are sized and shaped to engage with their counterpart (i.e., respective rod fastener) in a complementary manner.

Figure 3A:
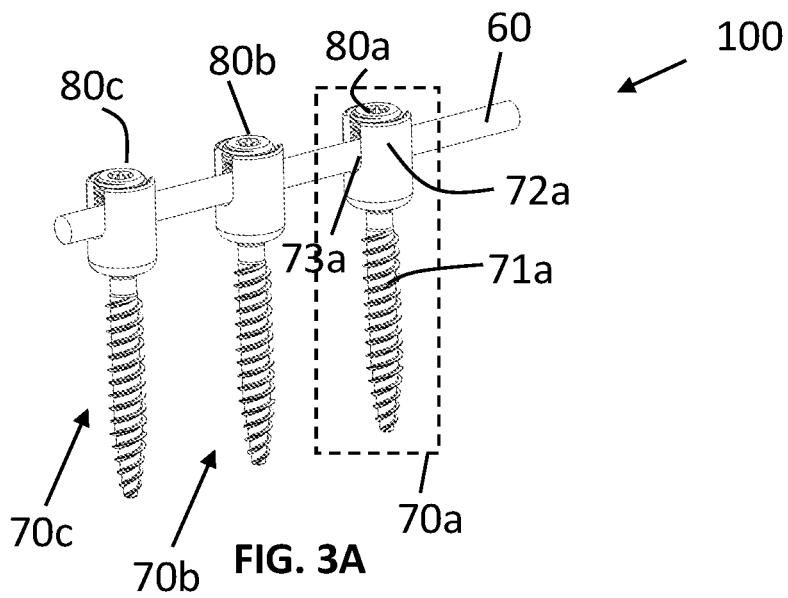
FIGS. 3A to 3N depict the process of elongating or extending an existing posterior spinal construct.
Figures 3B, 3C, 3D, 3E:
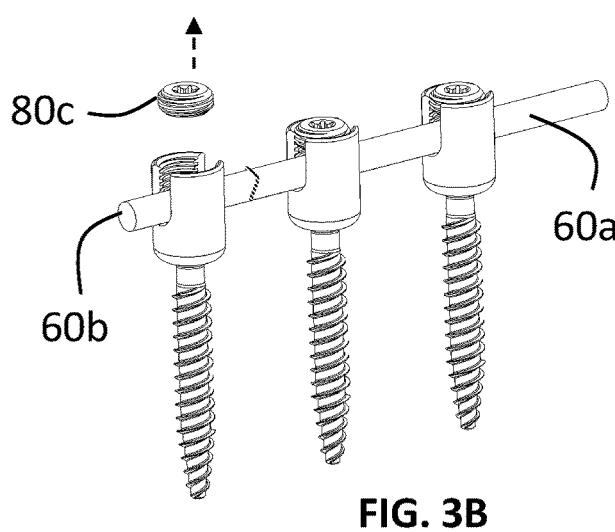
Figures 3F, 3G, 3H, 3I:
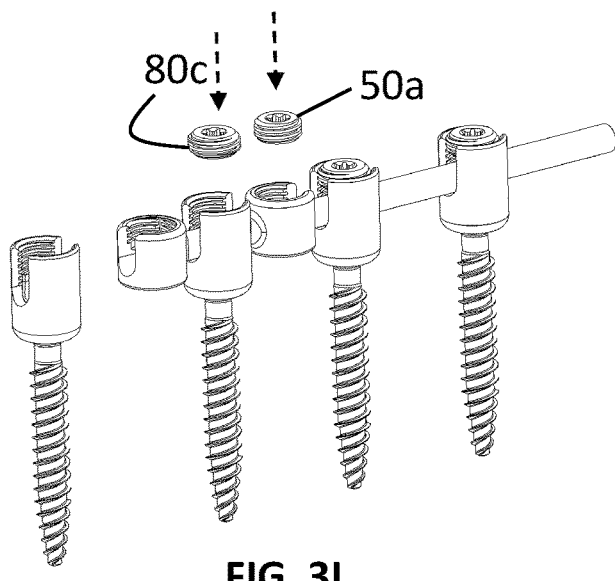
Figure 3J:
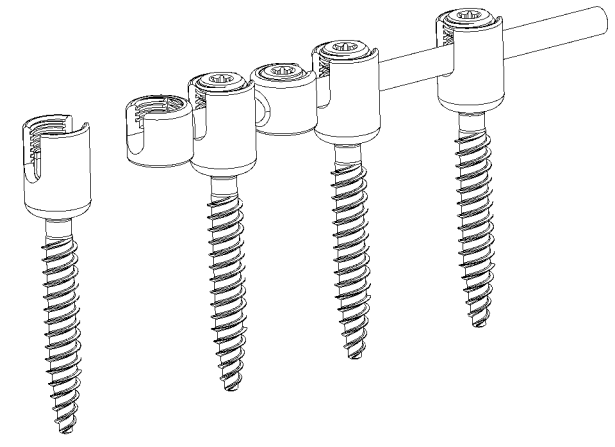
Figure 3K:
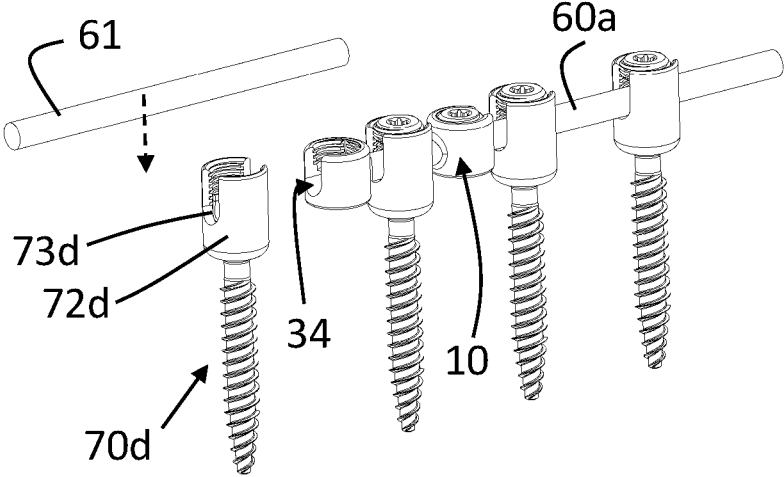
Figure 3L:
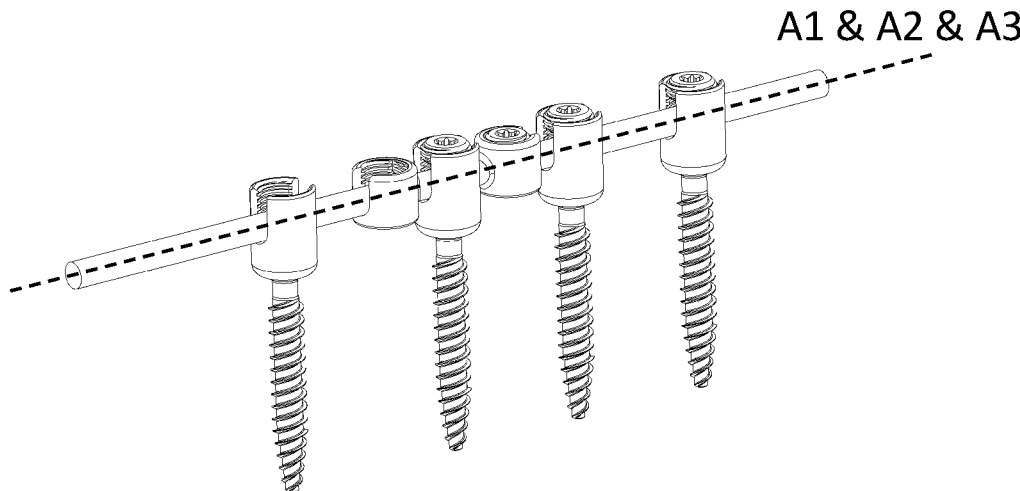
Figure 3M:
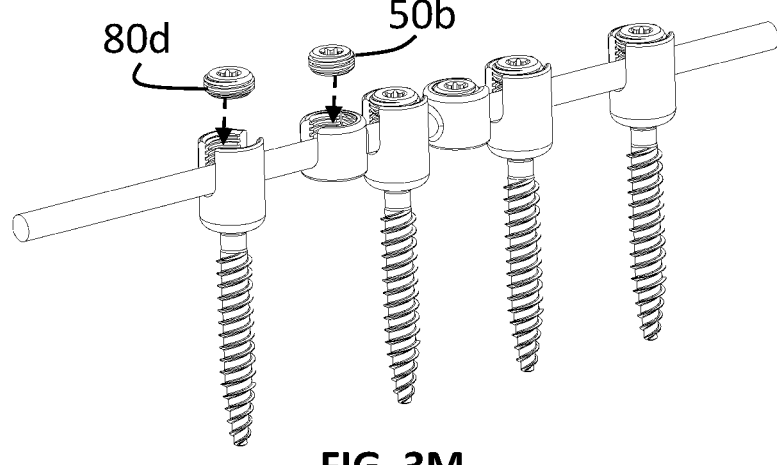
Figure 3N:
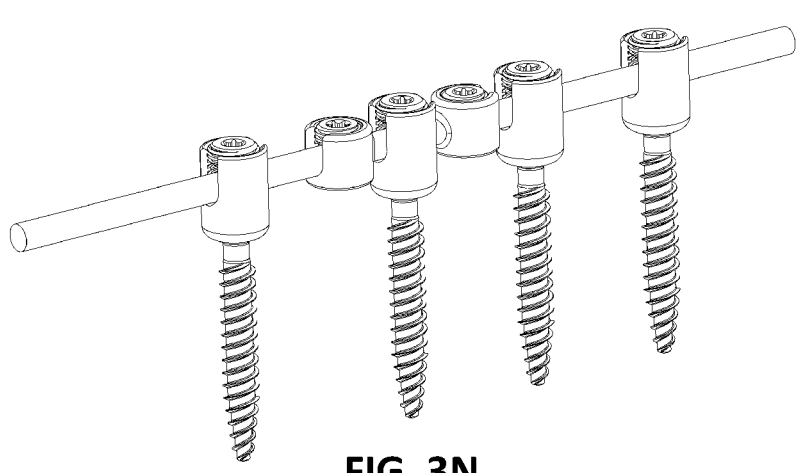

FIGS. 3A to 3N illustrate the steps of extending a posterior spinal construct 100. For illustration purposes, the spinal column is not shown. It is to be noted that the method as described below may also be applied to other bones instead. Furthermore, the method is applicable to rod connectors or connector implants comprising one head or two heads.

FIGS. 3A to 3N depict an example way of extending an in situ spinal construct by adding at least one bone fastener to an adjacent vertebral body and elongating the spinal construct by previously cutting the in situ rod between the last two in situ bone fasteners, removing the cut-off rod end, and assembling the spinal connector in the last in situ bone fastener.

FIG. 3A depicts a posterior spinal construct or system in place or in situ. Three bone fasteners are shown, a first bone fastener 70a, a second bone fastener 70b and a third bone fastener 70c. The bone fasteners are depicted as state-of-the-art pedicle screws, most commonly used for stabilising the posterior spine. The present example illustrates the extension of the posterior spinal system towards at least a fourth bone fastener (or spinal column vertebra).

The first bone fastener 70a comprises a first bone screw portion 71a and a first head portion 72a, including a first recess or tulip 73a sized and shaped to receive the rod 60. Similarly, the second and third bone fasteners 70b, 70c comprise, respectively, second and third bone screw portions 71b, 71c, second and third head portions 72b, 72c including second and third recesses 73b, 73c for receiving the rod 60. The rod 60 is rigidly fixated by a first setscrew 80a, a second setscrew 80b and a third setscrew 80c.

FIG. 3B depicts the cutting of the rod between the second and third bone fasteners 70b, 70c resulting in the rod 60 being separated in a rod portion 60a and a cut-off end 60b. FIG. 3B further shows the removal of the third setscrew 80c, thus allowing the removal of the cut-off end 60b. FIG. 3C depicts the posterior spinal construct after the previously described removal steps.

FIG. 3D depicts the addition of a fourth bone fastener 70d. The fourth bone fastener 70d comprises a fourth bone screw portion 71d and a fourth head portion 72d, including a fourth recess 73d, sized and shaped to receive a portion of the rod connector 10.

FIGS. 3E to 3H depict the engagement of the rod connector 10 with the third bone fastener 70c. In a first assembly step, the rod connector is brought forward to the posterior spinal construct and simultaneously engaged with the rod portion 60a and the third bone faster 70c. In order to assemble all the elements, the first and second top entrances 18, 38 are facing towards the posterior spinal construct 100 (i.e., facing downwards in FIG. 3E). The elongated bar 13 of the rod connector is simultaneously engaged into the third recess 73c, while one of the first and second pockets 14, 34 of the rod connector is engaged over the in situ rod portion 60a.

In a following step, the rod connector 10 is turned about its first central axis A1, until the first and second pockets 14 and 34 are facing upwards. This situation is shown in FIG. 3H. Alternatively, the pockets may be directed sideways or in any direction between the above directions. For the use of the system, the pockets should be facing in such a direction that the operating surgeon is able to insert the second rod 61, and is able to finally fixate the rod connector 10 to the second rod as well as to the rod portion 60a, by locking the rod fasteners 50a, 50b in place.

FIGS. 3I and 3J depict the placement of the third setscrew 80c and the first rod fastener 50a. It is to be noted that the setscrews and the rod fasteners are in this example substantially identical elements. The rod connector is now rigidly fixated to the rod portion 60*a* and the third bone fastener 70*c*.

FIG. 3K depicts the placement of the second rod 61 into the second pocket 34 of the rod connector and the fourth recess 73*d*. FIG. 3L depicts the second rod 61 in place, and the alignment of the central axes A1, A2, A3 according to the present example, where the second and third central axes A2, A3 are defined by the first and second rods 60, 61, respectively. FIGS. 3M and 3L depict the final fixation state of the whole construct. This state has been reached by tightening the second rod fastener 50*b* and the second setscrew 80*d* in place. The construct has now been extended by at least one bone fastener, or more specifically by a length corresponding to a distance between two bone fasteners.

Referring to FIGS. 4A to 4E, embodiments of a rod connector kit are shown. Anatomically, the natural spine decreases in size from the lumbar spine to the cervical spine (from the lower back to the neck). Therefore, when extending a system towards the cervical spine, instead of connecting rods of similar diameter, there is a need for connecting the system to smaller diameter rods. Inversely, when extending a system from the neck towards the thoracic or lumbar spine, there is a need for connecting the system to larger diameter rods. Therefore the rod connector as described in the present application can be sized and/or shaped in different sizes and/or shapes and can be used to connect rods of different diameters as well as rods of equal diameters.

Figure 4A:
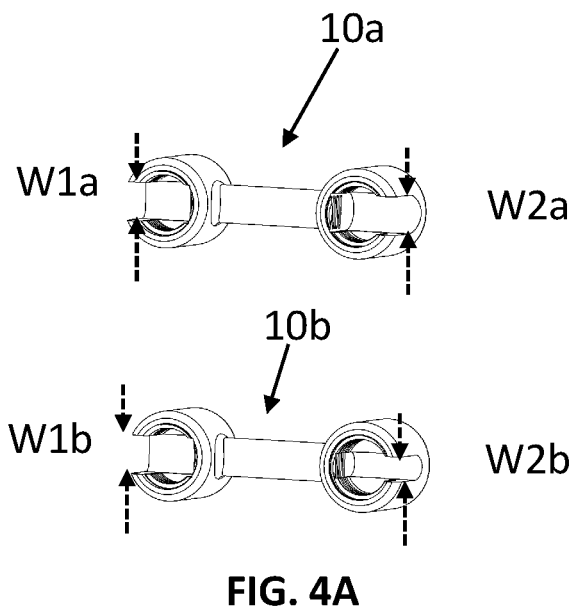
Figure 4B:
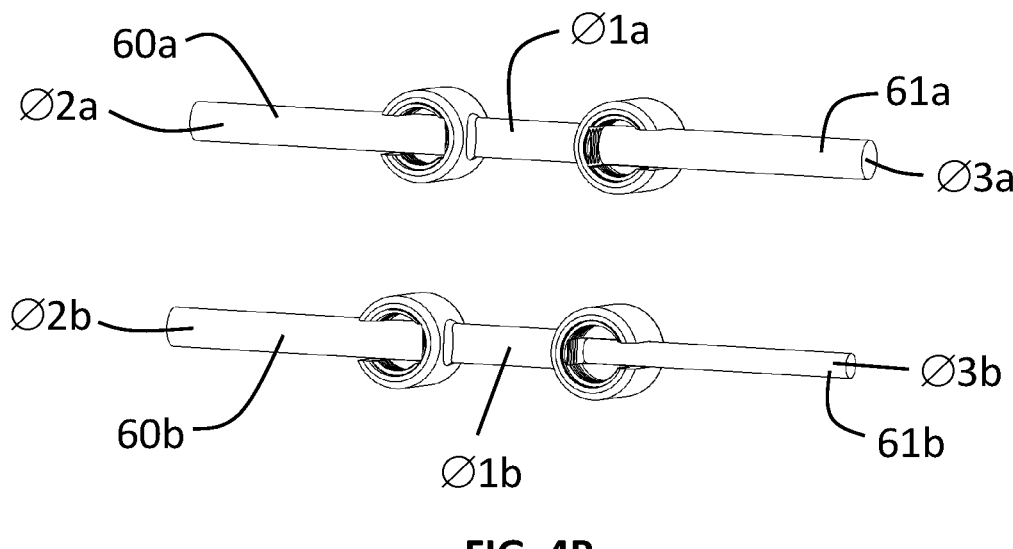

FIG. 4A shows two example rod connectors 10*a*, 10*b*. The rod connectors each include a first connector head 11 and a second connector head 31. One of the first connector heads 11 includes a first pocket 14 having a width W1*a*, while the other first pocket of the other first connector head 11 has a width W1*b*. The second connector heads 31 include second pockets 34 (one pocket per head) having widths W2*a* and W2*b*. In the present example, the first widths W1*a*, W1*b* are of equal size, and the second widths W2*a*, W2*b* are of different size. FIG. 4B shows the rod connectors 10*a*, 10*b* including an engaged rod. The outer diameters of the rods are sized and shaped to fit in a play free manner within the pockets, therefore the pocket widths are substantially equal to the rod diameters.

Most commonly, the size of the rod receiving pocket is referred to by the size of the rod it is intended to receive. Therefore, in the compatibility charts as shown in FIGS. 4C to 4E, which explain example kit structures, the rod diameters are referenced which engage in both the first and second connecting heads. The units given in FIGS. 4C to 4E are millimetres. FIG. 4C shows an example kit of different rod connectors to be used when extending a rod towards a rod of similar thickness. FIG. 4D shows an example kit of different rod connectors to be used when extending a system from a first rod to a second rod of smaller thickness. FIG. 4E shows an example kit of different rod connectors to be used when extending a system from a first rod to a second rod of greater thickness. The rod diameter and elongated bar diameter values as displayed in the tables of FIGS. 4C to 4E are typical standard diameter sizes in millimetres, as clinically commonly used. However, it is to be noted that the system is not limited to these sizes.

Figures 5F, 5G, 5H:
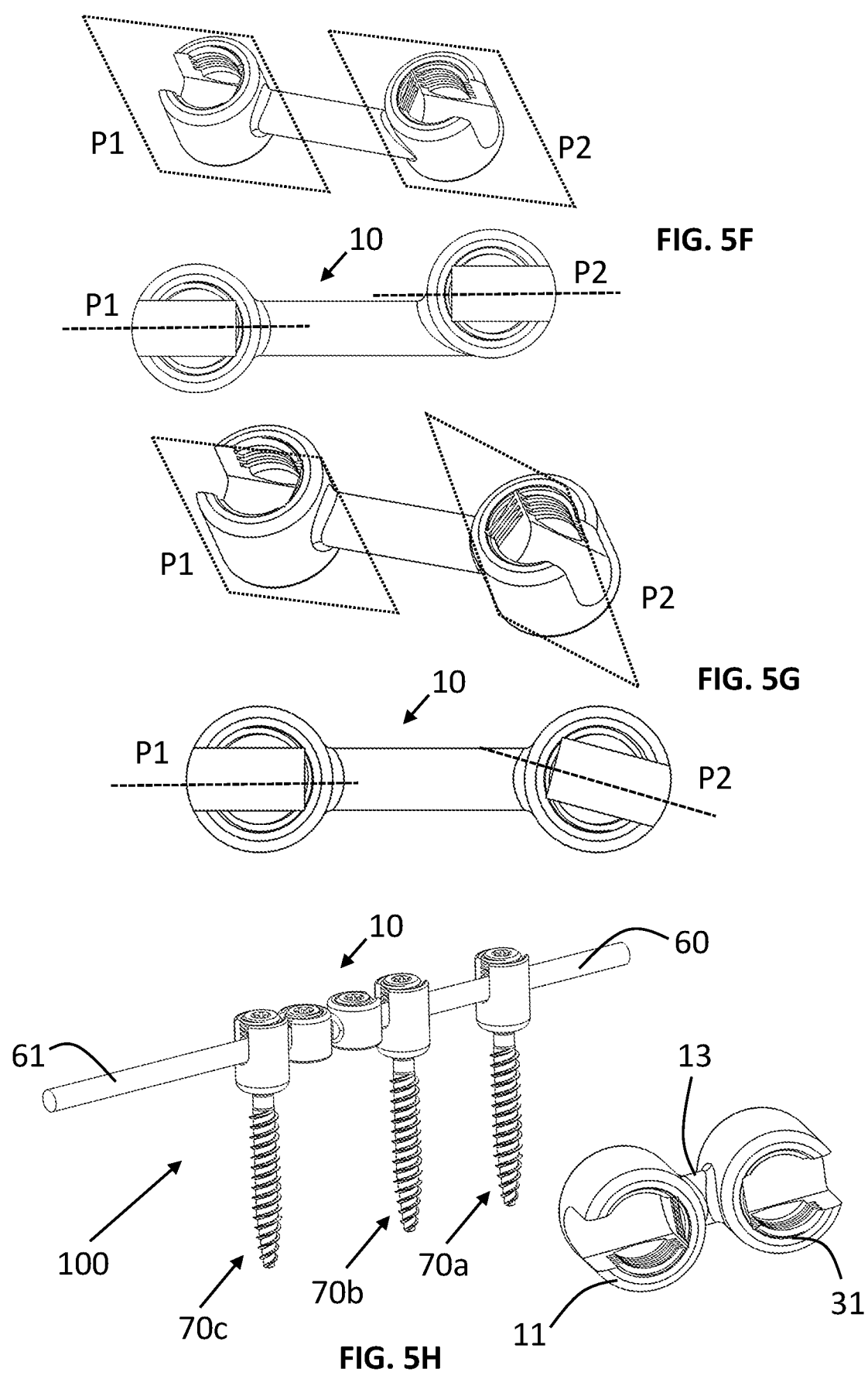
Figure 7A:
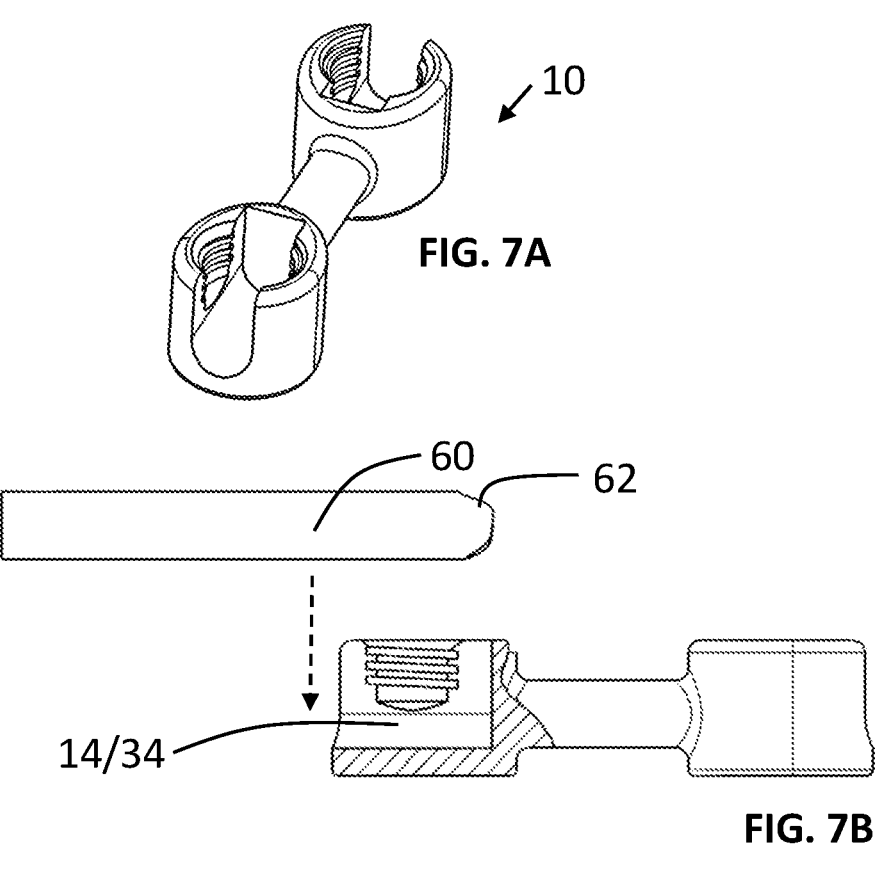
Figure 7B:
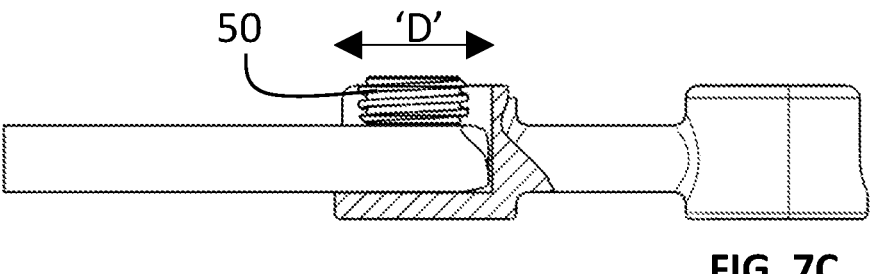
Figure 7D:
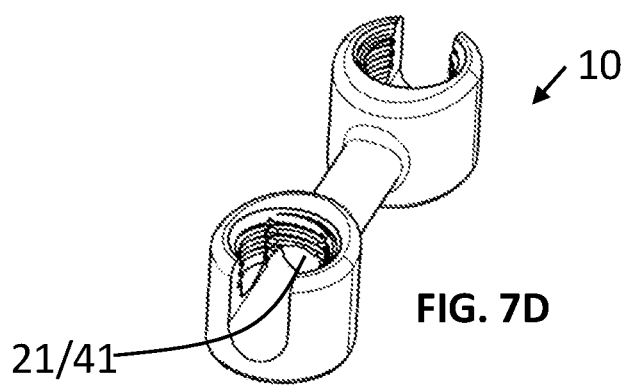
Figures 9A, 9B, 9C, 9D:
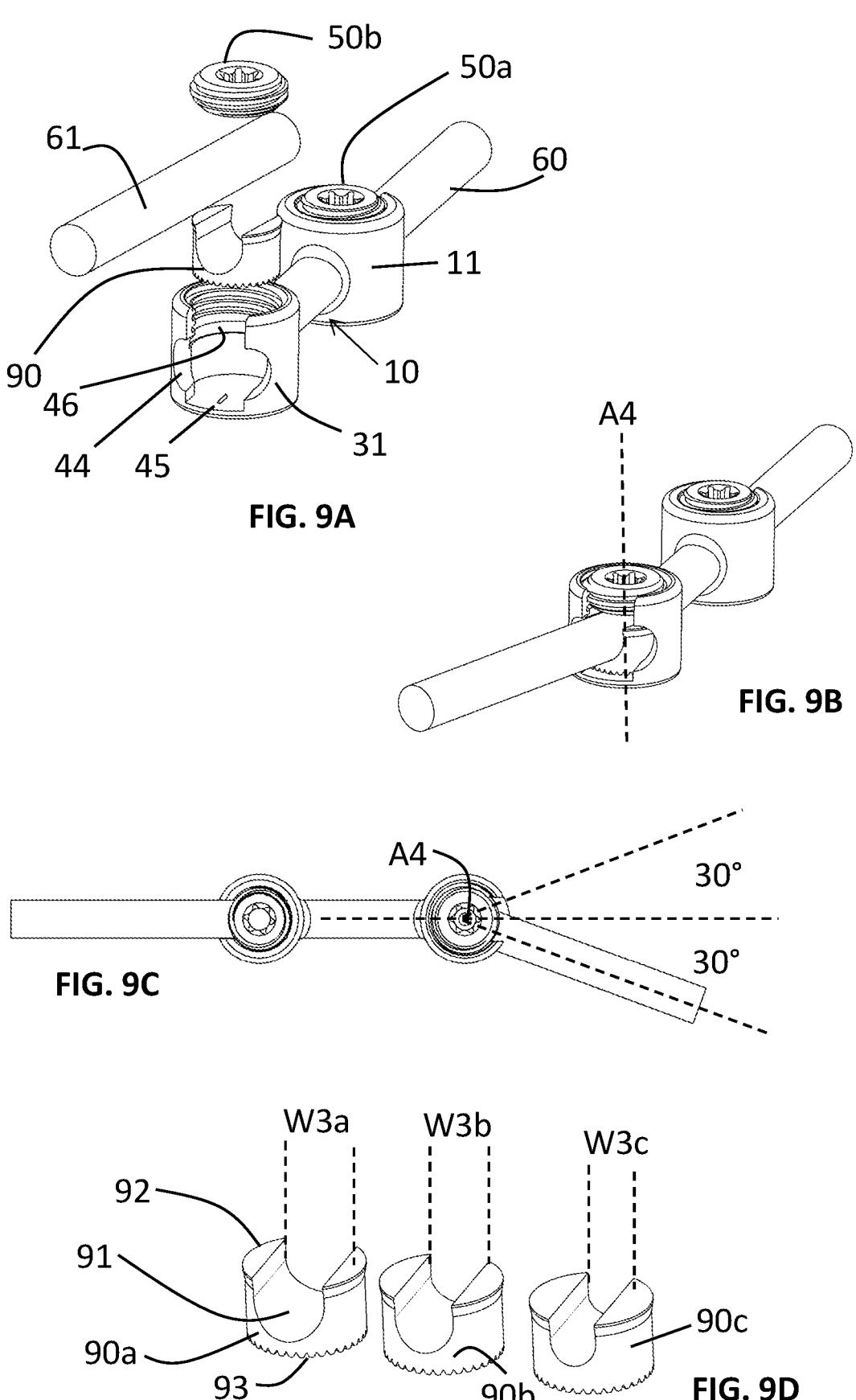
FIGS. 9A to 9D depict a variant of the rod connector wherein at least one end can rotate in at least one direction or plane.

Referring to FIGS. 5A to 5G, alternative designs of the rod connector are shown. FIG. 5A shows two rod connectors 10, where the elongated bars 13 have different lengths L1, L2. In the cases of greater distances between two consecutive bone fasteners, a longer elongated bar provides an easier way of bridging this distance. FIGS. 5B to 5D show alternative shapes of the pocket bottom seats 15, 35, such as a curved seat (i.e., a U-shaped seat), a triangular seat and a flat seat. FIG. 5E shows a modular version of the rod connector 10. The first connector head 11 and the second connector head 31 comprise, respectively, a first elongated bar portion 13*a* and a second elongated bar portion 13*b*, wherein these elongated bar portions are slidingly engaged in a telescope manner. As a result, the modular rod connector can be adapted in length, for fixation between two spinal rods. As shown, the first elongated bar portion 13*a* comprises a (longitudinal) slot forming a compliant structure. When placed within a bone fastener, upon tightening of a setscrew, the first elongated bar portion 13*a* is pressed against the second elongated bar portion 13*b*, and any movement between the bar portions is inhibited. FIG. 5F shows another design where the first and second central planes P1, P2 of the first and second pockets, respectively, are oriented in an offset manner. FIG. 5G shows yet another design where the first and second central planes P1, P2 of the first and second pockets, respectively, are oriented in an oblique manner. FIG. 5H shows an alternative design of the rod connector comprising a very short elongated bar 13 between the first and second connector heads 11, 31. The short rod connector can be used to connect two spinal rods, without any intermediate bone fastener between the first and second connector heads 11, 31. In one example, the bar has a length of 2 mm to 8 mm, or more specifically between 3 mm to 5 mm.

Referring to FIGS. 6A to 6D, a specific detail of the rod connector is shown. When spinal rods are intra-operatively customised to the patient anatomy, they are often cut by hand using a specific rod cutting instrument. The manual rod cutting often creates a small irregular edge 62 at the end of the rod 60. This edge may affect flush placement of the rod within the rod connector and therefore negatively affects the final fixation. To overcome this problem, at least one of the first and second pockets 14, 34 of the rod connector 10 may include a cavity or recess 21, 41 near the respective pocket end seat 16, 36 (i.e., at the end of the pocket which faces the elongated bar) and extending into the respective pocket bottom seat 15, 35. The cavity forms a clearance for any irregular edge of the spinal rod.

Referring to FIGS. 7A to 7E, a specific detail of the rod connector is shown. When spinal rods are intra-operatively customised to the patient anatomy, they are often cut by hand using a specific rod cutting instrument. The manual rod cutting often creates a small irregular edge 62 which is 'triangular shaped' at the end of the rod 60. This edge may affect flush placement of the rod within the rod connector and therefore negatively affects the final fixation. To overcome this problem, at least one of the first and second pockets 14, 34 of the rod connector 10 may include a cavity 21, 41 extending into the respective pocket end seat 16, 36. The cavity forms a clearance for any irregular edge of the spinal rod. Alternatively, the full pocket may have an increased length D, ensuring that the rod fastener (or setscrew) 50 is fully engaged with the rod 60. According to one example, a standard pocket length is at least 1.5 times the rod diameter it is intended to receive. According to the extended pocket configuration, the pocket length is at least 2 times the rod diameter it is intended to receive. It is to be noted that a longer pocket length provides higher stability, therefore a higher ratio is preferred.

Referring to FIGS. 8A and 8B, the rod connector 10 including side and front instrument pockets 22*a*, 22*b*, 23*a*, 23*b* 42*a*, 42*b*, 43*a*, 43*b* is shown. These pockets are in this example slots. The instrument pockets provide a means for grasping the rod connector with an instrument such as special pliers for handling and placement of the rod connector. The rod connector may comprise one or more of these instrument pockets.

Referring to FIGS. 9A to 9D, an alternative embodiment of a modular rod connector is shown. At least one of the connector heads 11, 31 comprises a rotatable insert 90, which can rotate about a fourth central axis A4, which is substantially perpendicular to the first central axis A1, and extends in the length direction (or parallel to it) of a bone fastener. The first and/or second end entrances 17, 37 comprise(s) at least a partial clearance 44, providing space for rotation of the connected spinal rod 60, 61 about the fourth axis A4.

The surgeon can assemble the desired rod connector configuration intra-operatively out of the individual components by selecting the appropriate insert 90a, 90b, 90c, 90x having a third rod receiving pocket width W3a, W3b, W3c, W3x, sized and shaped to receive the desired spinal rod (with a given diameter) in a substantially play free manner. For ease of assembly, the insert may include a rim 92 (i.e., a thickened or protruding section), which is sized and shaped to engage with a groove 46 within the respective rod connector head. The "rim in groove" connection will prevent the insert from disengaging or falling out of the respective pocket 14, 34, but will provide a rotational freedom.

According to the present example, the inserts 90, 90x comprise a first teeth structure 93 at the bottom end or side (i.e. at the end facing the bottom of the connector head), which is sized and shaped to engage width a second teeth structure 45, within the respective pocket of the rod connector. Now by tightening the rod fastener 50a, 50b, the spinal rod 60, 61 is pressed against the insert, which is pressed against the pocket bottom, and simultaneously the teeth structures will engage with each other and prevent any movement. The advantages of the modular rod connector are the increased flexibility to adapt the connector to the rod orientations and to the patient specific anatomy. This type of arrangement also reduces the number of the system components and thus the necessary component stock.

Figure 9E:
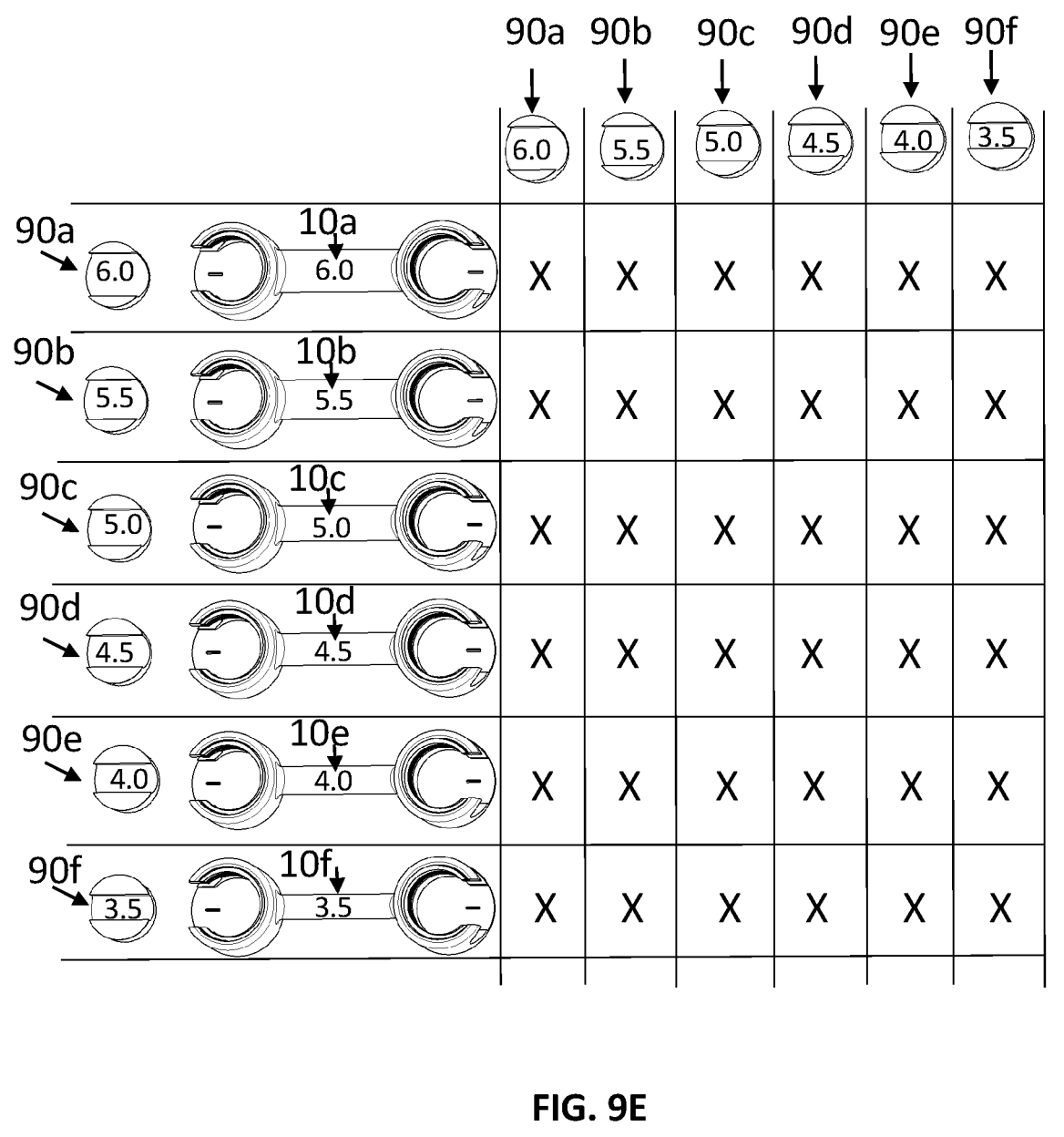

Referring to FIG. 9E, an example kit with modular rod connectors is shown. In this example, the kit with modular rod connectors as shown consists of six connectors 10a, 10b, 10c, 10d, 10e, 10f, each having an elongated bar of different diameter. Moreover, the kit includes 12 inserts 90a, 90b, 90c, 90d, 90e, 90f (with six different pocket sizes), each including a rod receiving pocket sized and shaped to receive a desired spinal rod (out of six different rod diameters). As depicted, by only having twelve separate items or inserts, 36 standard combinations can be created. The units given in FIG. 9E are millimetres.

Referring to FIGS. 10A to 10E, one further embodiment of the invention is shown. The rod connector 10 includes one connector head 11 only and the elongated bar 13 extending therefrom. According to one example, the elongated bar 13 has a length of at least 30 mm, or more specifically at least 40 mm.

Figures 10A, 10B, 10C, 10D:
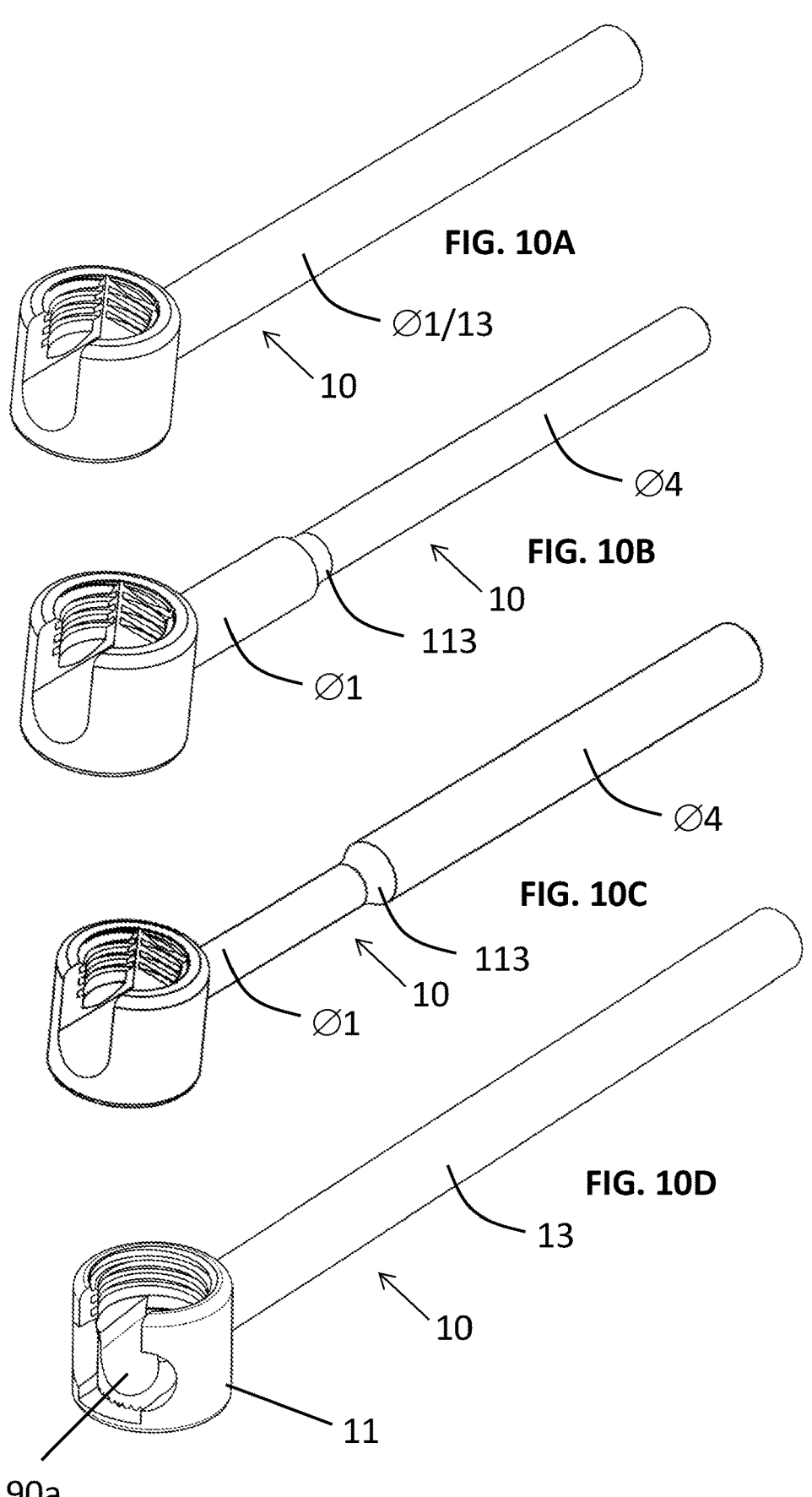

In the examples shown in FIGS. 10B and 10C, the elongated bar 13 includes a transition area 113 wherein the first diameter 'Øl' transitions into a fourth diameter 'Ø4', wherein the first and fourth diameters are of different sizes. FIG. 10B shows the transition of a larger diameter into a smaller diameter, for example to be used when extending a system from the lower back towards the neck. FIG. 10C shows the transition of a smaller diameter into a larger diameter, for example to be used when extending a system from the neck towards the lower back.

Referring to FIG. 10D, in analogy to the previous description in relation to FIGS. 9A to 9E, the connector head 11 comprises a rotatable insert 90, which can rotate about the fourth central axis A4, which is substantially perpendicular to the first central axis A1, and extends in the length direction (or parallel to it) of a bone fastener. The first end entrance 17 comprises at least a partial clearance 44, providing space for rotation of the connected spinal rod 60 about the fourth axis A4. Referring to FIG. 10E, the rod connector assembly according to the present embodiment, including bone fasteners, is shown. An advantage of the rod connector as described in FIGS. 10A to 10E is the reduced number of connection points. The disadvantage is the large portfolio needed to provide solutions for the possible spinal construct extension scenarios.

Referring to FIGS. 11A to 11H, yet another embodiment of the invention is disclosed. The rod connector 10 comprises at least one connector head 11, 31, where the respective top entrance extends in a direction or along a top entrance axis 170 which is orthogonal or substantially orthogonal to a respective connector head central axis 180. In the embodiments described earlier, the respective top entrance extended in a direction which was parallel to the respective connector head central axis. Contrary to the earlier embodiments, in the embodiment shown in FIGS. 11A to 11H, the opening of the respective connector head which is configured to receive the respective rod fastener, forms an enclosed shape (in this case a circle, but not limited to that). It is to be noted that in all the embodiments described so far, at least one of the pocket locking features 20, 40 is located substantially orthogonally to the top opening or more specifically to the surface defined by the top opening. As depicted, in this embodiment the rod fasteners 50 may be pre-assembled, prior to engaging the rod connector over an in-situ rod, eliminating this surgical step during surgery.

Figures 11E, 11F, 11G, 11H:
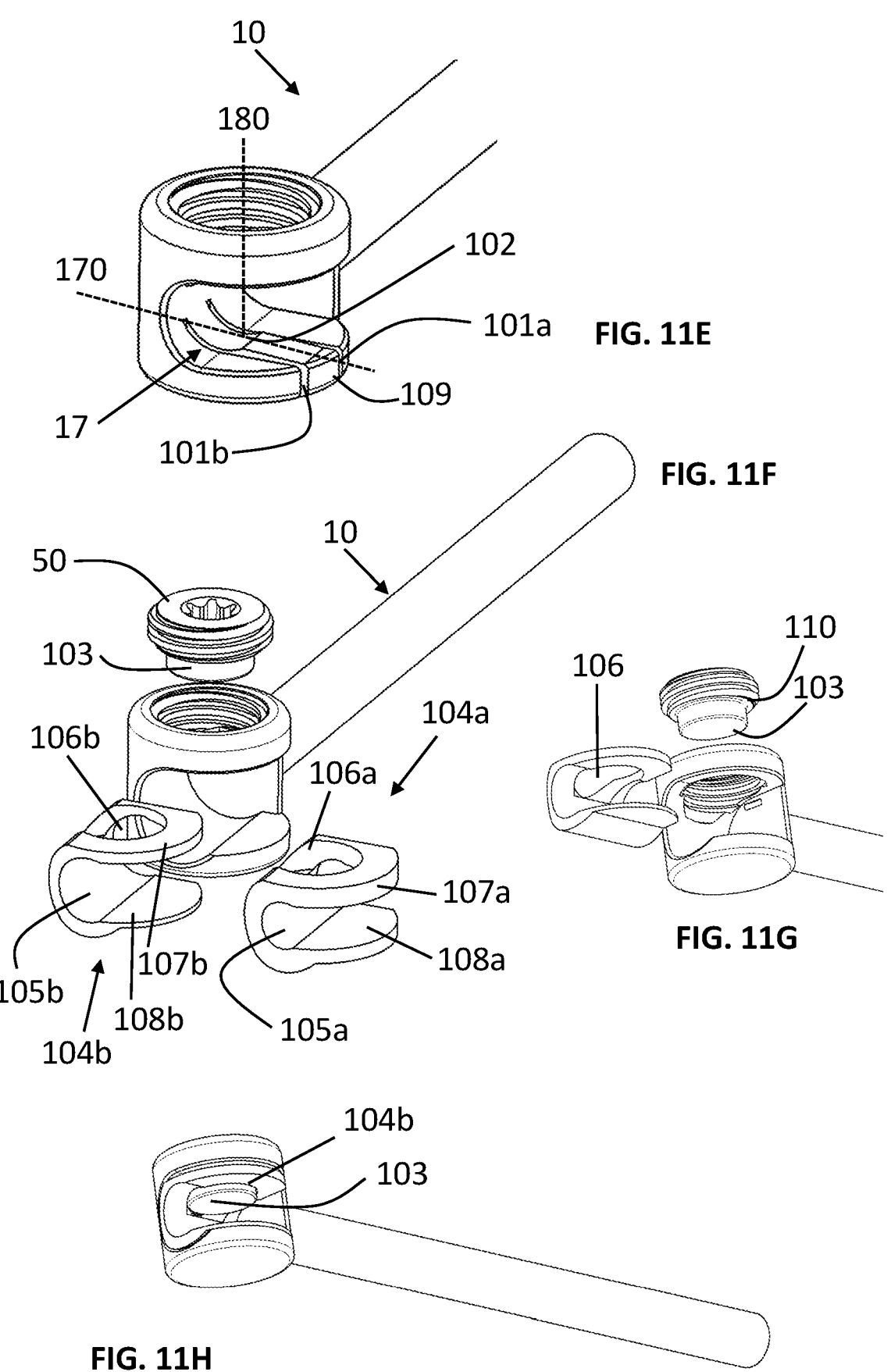

FIG. 11E depicts another specific embodiment. The first connector head 11 comprises a compliant structure 109, which is configured as a leaf spring feature, and bordered at at least two sides to a first and second groove 101a, 101b. The compliant structure further comprises a nose 102 protruding from the compliant structure main body, in this example upwards. In the present example, the nose is sized and shaped in a complementary manner to the rod 60 (not shown) the first connector head is intended to receive. Now, when inserting the rod 60, the compliant structure will snap around the rod, and provide first initial stability between the rod and the connector, before fully fixating the rod by means of tightening the rod fastener 50 (not shown).

Referring to FIGS. 11F, 11G and 11H, the rod connector 10 is shown comprising at least one first modular insert 104a, 104b. The modular insert comprises a passage, and in this example a keyhole shaped passage 105a, 105b sized and shaped to receive the rod 60 (not shown). The key hole shaped passage is open to at least one side, namely to the side of the top entrance of the pocket and to the side facing the end seat of the connector head. Furthermore, the modular insert is configured in a substantially complementary manner to the first pocket, and intended for insertion therein. The modular insert further comprises a hole 106a, 106b extending into the key hole shaped passage, sized and shaped for passage of a protrusion 103 of a rod fastener or setscrew as explained hereafter. The modular insert also comprises a top latch 107a, 107b and a bottom latch 108a, 108b. The top and bottom latches function as a leaf spring, functioning accordingly as the leaf spring, as described in connection with FIG. 11E. They will provide first initial stability between the rod and the connector, before fully fixating the rod by means of tightening of the rod fastener. Referring to the rod fastener 50, it comprises a protrusion 103, and extending away at the side opposite to the drive 42 of the rod fastener (i.e. the protrusion extends downwards in FIG. 11F). The protrusion is intended for direct engagement with the rod, before the setscrew base 110 will engage with the modular insert.

FIG. 11F depicts at least two modular inserts 104*a*, 104*b*, each having a differently sized key hole passage 105*a*, 105*b*. It is to be noted that by means of having differently sized insert passage, a kit is provided, wherein by assembling different modular inserts, the rod connector can be adapted to different sizes of rods.

As depicted in FIG. 11H, upon passage of the protrusion 103 through the hole 106, and upon tightening of the threadedly engaged rod fastener 50, the protrusion will engage against the rod 60 (not shown), the rod will engage against the modular insert, and the modular insert will engage against the pocket, and therefore the whole construct will be rigidly fixated. Furthermore, referring to the assembly steps of FIGS. 3A to 3N, according to the embodiment shown in FIGS. 11A to 11H, a rotation angle of about 60 degrees of the rod connector would be sufficient.

To summarise, one aspect of the present invention relates to a spinal rod connector assembly 94 for elongating an in situ spinal posterior rod system 100. The spinal rod connector assembly 94 comprises a rod connector 10 and at least one rod fastener 50*a*, 50*b*. The rod connector comprises a first connector head 11 and an elongated bar 13. The first connector head 11 comprises a first pocket 14 defined by a first pocket bottom seat 15, a first pocket end seat 16, and a first pocket side wall 19*a* or opposing first pocket side walls 19*a*, 19*b*. The first connector head 11 comprises a first end entrance 17, which is opposite to the first pocket end seat 16, or at least a portion of the first end entrance is opposite to the first pocket end seat, and a first top entrance 18 opposite to the first pocket bottom seat 15. The first pocket 14 is configured to directly receive, or to indirectly receive by means of a first insert 90, 104*a*, 104*b* in the first pocket 14, a first rod 60 of a first rod diameter. The first pocket 14 comprises a first pocket locking feature 20, wherein the at least one rod fastener 50*a*, 50*b* comprises a fastener locking feature 51*a* for engaging with the first pocket locking feature 20. The elongated bar 13 extends from a first connector head side, which is opposite to the first end entrance 17 or at least a portion of it. The elongated bar 13 is sized and shaped to be received by, or partially within, a bone fastener 70*a*, 70*b*, 70*c*, 70*d*. The above description may by analogy be applied to the second connector head. Furthermore, according to the embodiments described above, the greatest dimension of the elongated bar cross section in a bar plane perpendicular to an elongated bar length axis is smaller than the greatest dimension of the first and/or second connector head cross section in a connector head plane parallel to the bar plane. The bar cross section may be at most 20 mm, or more specifically at most 10 mm. The cross section dimension and shape is such that the bar 13 can be received in a bone fastener head and fixated therein. Thus, a space is proved between the first and second connector heads 11, 31 to allow a bone fastener head to be received in the space when engaged with the bar 13.

Another aspect of the present invention relates to a spinal rod connector assembly 94 for elongating an in situ spinal posterior rod system 100. The spinal rod connector assembly comprises a rod connector 10 and at least one rod fastener 50*a*, 50*b*, wherein the rod connector comprises a first connector head 11 and a second connector head 31. The first connector head comprises a first pocket 14 defined by a first pocket bottom seat 15, a first pocket end seat 16, and opposite first pocket side walls 19*a*, 19*b*, the first connector head comprising a first end entrance 17, at least a portion of which being opposite to the first pocket end seat 16, and a first top entrance 18 opposite to the first pocket bottom seat 15, the first pocket 14 being configured to directly receive, or to indirectly receive by means of a first insert 90, 104*a*, 104*b* in the first pocket, a first rod 60 of a first rod diameter. The second connector head comprises a second pocket 34 defined by a second pocket bottom seat 35, a second pocket end seat 36, and opposite second pocket side walls 39*a*, 39*b*. The second connector head comprises a second end entrance 37 at least a portion of which being opposite to the second pocket end seat, and a second top entrance 38 opposite to the second pocket bottom seat 35, the second pocket being configured to directly receive, or to indirectly receive by means of a second insert 90, 104*a*, 104*b* in the second pocket, a second rod 61 of a second rod diameter. The first and second pockets 14, 34 comprise a first pocket locking feature 20 and a second pocket locking feature 40, respectively, wherein the at least one rod fastener 50*a*, 50*b* comprises a fastener locking feature 51*a*, 51*b* for engaging with at least one of the first and second pocket locking features 20, 40, and wherein the first and second end entrances are located at opposite ends of the rod connector, and wherein the rod connector further comprises an elongated bar 13 connecting the first connector head 11 to the second connector head 31, and forming a space between the first and second connector heads 11, 31, and wherein the elongated bar 13 is sized and shaped to be received by a bone fastener 70*a*, 70*b*, 70*c*, 70*d*.

While the invention has been illustrated and described in detail in the drawings and foregoing description, such illustration and description are to be considered illustrative or exemplary and not restrictive, the invention being not limited to the disclosed embodiments. Other embodiments and variants are understood, and can be achieved by those skilled in the art when carrying out the claimed invention, based on a study of the drawings, the disclosure and the appended claims. New embodiments may be obtained by combining any of the above teachings. In the claims, the word "comprising" or "including" does not exclude other elements or steps, and the indefinite article "a" or "an" does not exclude a plurality. The mere fact that different features are recited in mutually different dependent claims does not indicate that a combination of these features cannot be advantageously used.

The invention claimed is:

1. A spinal rod connector assembly for elongating an in situ spinal posterior rod system, the spinal rod connector assembly comprising:
   a bone fastener;
   at least one rod fastener; and
   a rod connector that includes:
      an elongated bar; and
      a first connector head that includes:
         a first pocket defined by a first pocket bottom seat,
         a first pocket end seat,
         opposing first pocket side walls,
         a first end entrance, at least a portion of which is opposite to the first pocket end seat, and
         a first top entrance opposite to the first pocket bottom seat, the first top entrance defining a top side for the rod connector,
   wherein:
      the first pocket is configured to directly receive, or to indirectly receive by means of a first insert in the first pocket, a first rod defining a first rod central axis, the first pocket including a first pocket locking feature, the at least one rod fastener includes a fastener locking feature for engaging with the first pocket locking feature, the elongated bar extends from a first connector head side, which is opposite to at least a portion of the first end entrance, wherein the elongated bar has a cross-sectional diameter orthogonally to its longitudinal axis at most 10 mm and is sized and shaped to be received by the bone fastener, wherein the elongated bar has a circular or oval cross section orthogonally to the longitudinal axis of the elongated bar, providing rotational flexibility along the longitudinal axis of the elongated bar when received within the bone fastener, wherein the first top entrance and the first end entrance, which is open to the top side, allow the first rod to be engaged in the first pocket through the top side to allow the longitudinal axis of the elongated bar and the first rod central axis to be aligned when the first rod is engaged in the first pocket, and wherein the first end entrance allows the first rod to protrude from the first pocket in an assembled state of the spinal rod connector assembly when the longitudinal axis of the elongated bar and the first rod central axis are aligned, wherein the bone fastener comprises a head portion including a recess, and wherein the elongated bar is received in the recess for rigidly fixating the rod connector to the bone fastener in the assembled state of the spinal rod connector assembly, a second connector head connected by the elongated bar to the first connector head, the elongated bar forming a space between the first and second connector heads, the second connector head including:

a second pocket defined by a second pocket bottom seat, a second pocket end seat, opposing second pocket side walls, a second end entrance, at least a portion of which being opposite to the second pocket end seat, and a second top entrance opposite to the second pocket bottom seat, the second pocket being configured to directly receive, or to indirectly receive by means of a second insert in the second pocket, a second rod, wherein:

the second pocket includes a second pocket locking feature, and the first and second end entrances are located at opposite ends of the rod connector, wherein:

the first connector head defines a first central plane extending between the first pocket bottom seat and the first top entrance, the second connector head defines a second central plane extending between the second pocket bottom seat and the second top entrance, and the first and second central planes are oriented at an acute angle with respect to each other, or at least one of the first and second central planes is located offset with respect to the longitudinal axis of the elongated bar.

2. The spinal rod connector assembly according to claim 1, wherein:

a minimal first distance between the first pocket side walls defines a first pocket width, a minimal second distance between the second pocket side walls defines a second pocket width, and the first and second pocket widths are equal.

3. The spinal rod connector assembly according to claim 2, wherein:

a minimal first distance between the first pocket side walls defines a first pocket width, a minimal second distance between the second pocket side walls defines a second pocket width, and the first and second widths are unequal.

4. The spinal rod connector assembly according to claim 1, wherein the first pocket locking feature extends towards the first pocket bottom seat from the first top entrance.

5. The spinal rod connector assembly according to claim 2, wherein:

a minimal first distance between the first side walls defines a first pocket width, a minimal second distance between the second side walls defines a second pocket width, and at least one of the first and second widths is substantially equal to an elongated bar diameter.

6. The spinal rod connector assembly according to claim 1, wherein:

the first pocket locking feature is configured as an internal thread, the fastener locking feature is shaped as an external thread, or vice-versa, and the first pocket locking feature and the fastener locking feature are shaped to engage in a complementary manner.

7. The spinal rod connector assembly according to claim 1, wherein:

the first connector head defines a first central plane extending between the first pocket bottom seat and the first top entrance, and the first central plane is substantially collinearly aligned with the longitudinal axis of the elongated bar.

8. The spinal rod connector assembly according to claim 1, wherein the rod connector comprises a first elongated bar portion and a second elongated bar portion forming a telescopic structure.

9. The spinal rod connector assembly according to claim 1, wherein the elongated bar comprises a transition area between two bar sections having different diameters.

10. The spinal rod connector assembly according to claim 1, wherein the greatest dimension of an elongated bar cross section in a first plane perpendicular to the longitudinal axis of the elongated bar is smaller than the greatest dimension of a first connector head cross section in a second plane parallel to the first plane.

* * * * *